(12) United States Patent
Akduman

(10) Patent No.: US 12,070,387 B2
(45) Date of Patent: *Aug. 27, 2024

(54) STAPHYLOMA SUPPORTING DEVICE AND METHOD FOR MODIFYING THE AXIAL LENGTH AND CURVATURE OF AN EYE

(71) Applicant: LA EYE LLC, St. Louis, MO (US)

(72) Inventor: Levent Akduman, Richmond Heights, MO (US)

(73) Assignee: LA EYE LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/359,744

(22) Filed: Jul. 26, 2023

(65) Prior Publication Data

US 2023/0363888 A1    Nov. 16, 2023

Related U.S. Application Data

(63) Continuation of application No. 17/759,249, filed as application No. PCT/US2022/070733 on Feb. 18, 2022, now Pat. No. 11,751,989.

(60) Provisional application No. 63/200,189, filed on Feb. 19, 2021.

(51) Int. Cl.
*A61F 9/007* (2006.01)
*A61F 2/14* (2006.01)

(52) U.S. Cl.
CPC ............ *A61F 2/14* (2013.01); *A61F 9/00727* (2013.01); *A61F 2220/0008* (2013.01)

(58) Field of Classification Search
CPC .................................................... A61F 9/00727
See application file for complete search history.

(56) References Cited

U.S. PATENT DOCUMENTS

| 7,008,396 B1 | 3/2006 | Straub |
| 2003/0139808 A1 | 7/2003 | Shahinpoor et al. |
| 2004/0254420 A1 | 12/2004 | Ward |
| 2014/0074234 A1 | 3/2014 | Reus et al. |
| 2019/0175753 A1 | 6/2019 | Sun |
| 2020/0197725 A1 | 6/2020 | Marsteller |
| 2021/0290434 A1 | 9/2021 | Chan |

FOREIGN PATENT DOCUMENTS

| FR | 2354089 A | 2/1978 |
| SU | 1537274 A1 | 1/1990 |
| WO | WO-02067688 A1 | 9/2002 |
| WO | WO-2017033081 A1 | 3/2017 |

*Primary Examiner* — Javier G Blanco
(74) *Attorney, Agent, or Firm* — SALIWANCHIK, LLOYD & EISENSCHENK

(57) ABSTRACT

Surgical implants and methods to improve, support, or help to preserve vision by altering the axial length or curvature of an eye are provided. Staphyloma supporting devices or implants can be of unitary construction from a single base material such as titanium alloy and can have a macular indenter plate wider than the implant body and an anchor structure wider than the macular indenter plate. A compound concavity scleral contact surface can approximate the outer surface of the eye with an anterior radius of curvature and can restore macular shape and axial length with a second posterior radius of curvature that can be less than the anterior radius of curvature.

20 Claims, 7 Drawing Sheets

STAPHYLOMA SUPPORTING DEVICE AND METHOD FOR MODIFYING THE AXIAL LENGTH AND CURVATURE OF AN EYE

CROSS-REFERENCE TO RELATED APPLICATIONS

The present application is a continuation of U.S. application Ser. No. 17/759,249, filed Jul. 21, 2022, which is the National Stage of International Application Number PCT/US2022/070733, filed Feb. 18, 2022, which claims the benefit of U.S. Provisional Application Ser. No. 63/200,189, filed Feb. 19, 2021, which is hereby incorporated by reference herein in its entirety, including any figures, tables, nucleic acid sequences, amino acid sequences, or drawings.

BACKGROUND OF THE INVENTION

In myopia (near-sightedness), front to back (anteroposterior AP) length of the eye is increased. AP length of the eye is normally 22 mm to 24 mm (average 23 mm). Each mm additional elongation gives 3 diopters of refractive error to the eye. Besides the refractive error, when the AP length is longer than normal, the contents of the eyeball will stretch to fit the larger space created inside. One structure inside the eye that ends up stretching to fit is the retina. The retina is the nerve layer inside that makes the picture and sends it to the brain. The retina covers the inside of the back of the eye like a wallpaper covering the wall inside the house. In the case of the wall of the eye bulging out in the back, the retina inside can stretch and form a hole (myopic macular hole) or split in its layers (myopic macular schisis) in the middle, central part of the retina, also referred to as the macula. Macular holes can also occur in normal length eyes. Surgical treatments for a macular hole include placement of intraocular gas with a surgery called vitrectomy to push the hole closed. In the case of high myopia, the retina is so stretched that the hole will not easily close. Extraocular implants have been designed to push in from the outside of the eye, but bulk and complexity have limited their utility. Indenting the eye from outside with a surgical technique or an implant helps to correct myopic macular schisis as well as myopic macular holes.

The normal eye is practically round and/or spherical. The majority of the human population have as the size of the eye a spherical ball with a diameter in the range of 22 mm to 24 mm. In the front part of the eye, the cornea and the natural crystalline lens focus the image on the retina. If the eye is too long (e.g., longer than 24 mm), the front structures can focus the image in front of the macula, and the image falling on the retina can be blurred. Placing glasses in front of the eye or cutting and reshaping the cornea with laser (e.g., laser in-situ keratomileusis or LASIK) will change the refraction power of the front of the eye to place the image on the macula. A diagnostic test can measure the refractive error in an eye and the diameter (e.g., anteroposterior length or axial length of the eye.) Simple refraction for glasses or an autorefractometer will measure the refractive error.

High myopia has been said to have a prevalence of 1.7-2% in the general population of the USA and is especially common in Asia. In Japan, high myopia reportedly affects 6-18% of the myopic population and 1-2% of the general population.

Myopia has been reported as the most common ocular disorder worldwide, and the leading cause of visual impairment in children, with its incidence increasing rapidly. In 2010, an estimated 1.9 billion people (27% of the world's population) were myopic, and 70 million of them (2.8%) had high myopia. These numbers are projected to rise to 52% and 10%, respectively, by 2050.

Myopia is a major public health concern in many East Asian countries, where the condition affects 80% to 90% of high school graduates. Of these individuals, 10% to 20% have sight-threatening pathologic myopia.

Vision impairment related to myopia has a significant economic impact and a significant effect on quality of life regarding patients' physical, emotional, and social functioning. Scientists have estimated the loss in world productivity caused by uncorrected myopic refractive error in 2004 to be 268.8 billion international dollars and the cost of addressing this problem to be US$28 billion.

Pathologic myopia (prevalence 0.9%-3.1%) is particularly devastating. It confers an increased risk of cataract development, retinal detachment, glaucoma, and even blindness. The prevalence of choroidal neovascularization in affected individuals is reported to be 5.2% to 11.3%, and macular holes can occur in 6% to 8% of patients. The peripapillary regions are distorted by mechanical stretching of the globe in patients with increased axial lengths, and this can lead to glaucoma and visual field loss. The rapidly increasing incidence of myopia combined with its significant social and economic burdens have spurred research on causal factors, possible treatments, and efforts at prevention.

BRIEF SUMMARY OF THE INVENTION

In one aspect the present invention provides a unitary rigid ophthalmic surgical implant or staphyloma supporting device for improving vision in a patient by restoring the natural curvature and natural axial length of an eye. The eye, similar to a ball, has a convex outer scleral surface (the middle or side region of which can be referred to as the equator of the eye) and a concave inner surface. The implant can have a plate having a concave scleral mating surface configured to restore the natural curvature of a posterior portion of the eye, an anchor having a concave scleral mating surface configured to approximate the natural curvature of the more anterior portion of the eye, and a body having a continuous and smooth concave scleral mating surface connecting the plate to the anchor. The implant can have a total implant length less than the natural axial length of the eye. The width of the body can be less than the width of the plate and less than the width of the anchor. The width of the anchor can be greater than the width of the plate and the width of the body. In some embodiments the plate thickness, the body thickness, and the anchor thickness are each uniform and about equal.

In another aspect the invention provides an anchor having a first anchor point central to the body, a second anchor point lateral to the body and anterior to the first anchor point, and a third anchor point lateral to the body and anterior to the first anchor point such that a single straight line cannot pass between the first anchor point, the second anchor point, and the third anchor point. The anchor can also include a first arm connecting the second anchor point to the body and having a first arm width less than the body width, and a first arm length less than the body length; and a second arm connecting the third anchor point to the body and having a second arm width less than the body width and a second arm length less than the body length. The first arm and the second arm can form a symmetric Y shape with respect to the body.

Alternatively, the invention provides an anchor having a first anchor point central to the body, a second anchor point lateral to the body and posterior to the first anchor point, and a third anchor point lateral to the body and posterior to the first anchor point such that a single straight line cannot pass between the first anchor point, the second anchor point, and the third anchor point. The anchor can also include a first arm connecting the second anchor point to the body and having a first arm width less than the body width, and a first arm length less than the body length; and a second arm connecting the third anchor point to the body and having a second arm width less than the body width and a second arm length less than the body length. The first arm and the second arm can form a symmetric Y shape with respect to the body.

Alternatively, the anchor can include one or more round, circular, arcuate, polygonal, triangular, rectangular, square, pentagonal, hexagonal, asymmetric, symmetric, lobed, or irregular shaped arm or arms connecting one or more anchor points to the body. In certain embodiments the width of an anchor arm can be the same, less than, or greater than a width of the body.

In certain embodiments a second anchor point lateral to the body, and a third anchor point lateral to the body are on opposite lateral sides of the body. In certain embodiments a second anchor point lateral to the body, and a third anchor point lateral to the body are on the same lateral side of the body. In certain embodiments a second anchor point central to the body, and a third anchor point lateral to the body are provided. In certain embodiments a second anchor point central to the body, and a third anchor point central to the body are provided. Certain embodiments can be provided without a first anchor point, or with a first anchor point that is not central to the body and in such embodiments, certain references to a first anchor point herein can be applied instead to a lateral, medial, or other specified point on the body (e.g., to the intersection of the midlines of two anchor arms, or to the point formed by the intersection of an outer surface from each of two respective anchor arms, or by the intersection of an anchor arm with an implant body.

In any of the above embodiments, anchor points can be defined, placed, required, or measured such that a single straight line cannot pass between a first anchor point, a second anchor point, a third anchor point. Alternatively, anchor points can be defined, placed, required, or measured such that a single straight line can pass between a first anchor point, a second anchor point, and a third anchor point. In certain embodiments the above referenced lines can be defined, placed, required, or measured to pass or not pass through any part of the diameter, length, or width (as appropriate) of each anchor point. Alternatively, the above referenced lines can be defined, placed, required, or measured to pass or not pass through the center, origin, or base (as appropriate) of each anchor point.

In yet another aspect the present invention provides a rigid unitary implant of consistent or variable thickness having a concave scleral contact surface progressing from a first radius of curvature along a posterior macular indenter to an advantageously larger second radius of curvature at an anterior scleral anchor with a tangentially smooth transition therebetween; the first radius providing a smooth and more aggressive correction to restore the natural length and/or shape of the eye, the second radius providing an improved mating to an anterior surface of the eye, and the tangentially smooth transition providing a more natural alignment of the outer surface of the eye between the two curvatures.

Alternatively, the second radius of curvature at an anterior scleral anchor can advantageously be smaller than the first radius of curvature along a posterior macular indenter, the first radius providing a more gentle correction to restore the natural length and/or shape of the eye, the second radius providing an improved mating to an anterior surface of the eye, and the tangentially smooth transition providing a more natural alignment of the outer surface of the eye between the two curvatures.

The tangentially smooth transition can occur at any point along the body of the implant (e.g., proximal the plate, ⅓ of the arcuate distance from the plate towards the anchor, ½ of the arcuate distance from the plate towards the anchor, ⅔ of the arcuate distance from the plate towards the anchor, proximal the anchor, or any fractional amount therebetween; e.g., anterior to a point of scleral fixation where the body can be preliminarily attached to the scleral tissue while allowing AP adjustment of the implant to restore the eye, posterior to a point of scleral fixation, or proximal to a point of scleral fixation.

Alternatively, the second radius of curvature at an anterior scleral anchor can be equal to the first radius of curvature along a posterior macular indenter; the equal radii advantageously providing a more natural fit along the exterior surface of the sclera, simplified surgical implantation, and improved ease of manufacture.

In yet another aspect the invention provides surgical methods for fixation of a rigid, curved ophthalmic staphyloma supporting device 3 mm to 10 mm behind the limbus with the concave scleral mating surface of the implant in intimate contact with the scleral surface of the eye beneath the conjunctiva in the inferotemporal or superotemporal quadrant of an eye at a desired position to restore a more natural curvature and a more natural axial length of the eye.

Placing an implant in accordance with the teachings of the subject invention for the purpose of increasing the success rate of macular hole closure in a high myopic eye has many advantages. The subject invention shortens the eye and corrects the refractive error. In cases of myopic macular schisis, certain embodiments can reduce the existing splitting of the layers and also inhibit formation of a new schisis. Although the macular hole and macular schisis are relatively rare conditions (whether in myopic or normal size eye), myopia is very common. It is estimated that there are approximately 24 million people in the USA with myopia of −6.00 diopters or higher (called high myopia).

The implant of the subject invention can shorten the AP length of the eye, bringing down the above −6.00 Diopters to near normal. There are high myopic patients with the eyes even as long, or longer than 30 mm in AP length. One goal of surgery placing the implant in high myopic eyes is to modify the axial length. Doing that will address the need for glasses (e.g., wearing no glasses or much thinner glasses after the surgery) can make the patients eligible for LASIK surgery for residual refractive error (some patients are not eligible for LASIK surgery if the dioptric correction need is too high, since the corneal tissue to be removed with LASIK may not be acceptable).

There are also complications other than the macular hole and macular schisis that can occur in high myopic patients due to the extreme stretching of the retina inside the eye, including choroidal neovascular membranes and increased tendency to retinal detachment. These are serious complications that can result in legal or total blindness. Placing an implant of the subject invention to halt or decrease the elongation of the eye has multiple beneficial effects.

DETAILED DESCRIPTION OF THE INVENTION

Figure 1:
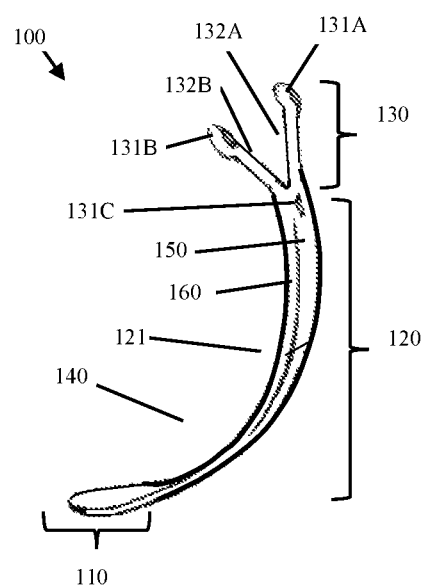
FIG. 1 shows a three-dimensional representation of one embodiment of a unitary rigid ophthalmic surgical implant in accordance with the subject invention.

Embodiments of the subject invention provide implants (e.g., unitary rigid ophthalmic staphyloma supporting device surgical implants) for improving vision in a patient (e.g., by restoring the natural curvature and/or natural axial length of an eye.) Implants can include a plate having a concave scleral mating surface (e.g., a surface configured to restore the natural curvature of a posterior portion of the eye), an anchor having a concave scleral mating surface (e.g., a surface configured to approximate the natural curvature of an anterior portion of the eye), and a body having a surface (e.g., a continuous and smooth concave scleral mating surface) connecting the plate to the anchor.

The eye being restored can have a natural linear axial length (e.g., between 22 mm and 24 mm natural axial length of the eye) and the implant can have a total linear implant length (e.g., measured in a straight line from a posterior end of the implant to an anterior end of the implant) that is less than the natural axial length of the eye (e.g., a total linear implant length less than 26 mm, or less than 25.5 mm, or less than 25 mm, or less than 24.5 mm, or less than 24 mm, or less than 23.5 mm, or less than 23 mm, or less than 22.5 mm, or less than 22 mm, or less than 21.5 mm, or less than 21 mm, or less than 20.5 mm, or less than 20 mm, or less than 19.5 mm, or less than 19 mm, or less than 18.5 mm, or less than 18 mm, or increments of any of the foregoing.)

Prior to surgery, the eye being restored can have a deformed, measured, pre-surgical axial length (and the implant can have a total linear implant length less than the deformed axial length of the eye.) Following surgery, the eye being restored can have a restored axial length (and the implant can have a total linear implant length less than the restored axial length of the eye; alternatively less than the pre-surgical or post-surgical measured axial length of the eye.)

In certain embodiments the deformed axial length of the eye can be measured before and/or during surgery and an implant can be selected having a total linear implant length less than 99% of the deformed axial length of the eye, alternatively less than 95% of the deformed axial length of the eye, alternatively less than 90% of the deformed axial length of the eye, alternatively less than 85% of the deformed axial length of the eye, alternatively less than 80% of the deformed axial length of the eye, alternatively less than 75% of the deformed axial length of the eye, alternatively less than 70% of the deformed axial length of the eye, or increments of any of the foregoing.

In certain embodiments the deformed axial length of the eye can be measured before and/or during surgery, a desired corrected axial length of the eye can be determined, and an implant can be selected having a total linear implant length less than 99% of the desired axial length of the eye, alternatively less than 95% of the desired axial length of the eye, alternatively less than 90% of the desired axial length of the eye, alternatively less than 85% of the desired axial length of the eye, alternatively less than 80% of the desired axial length of the eye, alternatively less than 75% of the desired axial length of the eye, alternatively less than 70% of the desired axial length of the eye, or increments of any of the foregoing.

Any suitably biocompatible implant material can be used to form certain embodiments of the subject invention. Polymers including but not limited to ultra-high molecular-weight polyethylene (UHMWP), high-density polyethylene (HDP), polymethyl methacrylate (PMMA) or other methacrylates, silicone (polysiloxanes), or VICRYL® (polyglactin 910) can be employed as primary materials, coatings, covers, cushions, meshes, bags, or liners with certain embodiments of the subject invention. When the implant includes metallic materials, suitable metals can include surgical grade stainless steel (e.g., 316L), cobalt-chromium (Co—Cr) alloys, pure commercial or surgical grade titanium (Ti), nickel-titanium alloy (nitinol), or other titanium alloys. Other metals, such as gold, platinum, silver, iridium, tantalum, and tungsten can be used. Metals can be employed as primary materials, coatings, covers, or liners with certain embodiments of the subject invention. Implants can be wholly, or partially metallic, bimetallic (e.g., constructed from two different metals), or non-metallic. Surface coatings such as titanium oxide or anodized finishes can be advantageously employed. Ceramics including aluminum oxide, calcium phosphates, zirconium oxide (Zirconia), and silicon oxide (Silica) can be used. Ceramics can be employed as primary materials, coatings, covers, or liners with certain embodiments of the subject invention. Natural or synthetic biological materials including autograft, allograft, xenograft, synthetic tissue substitutes, and cultured or engineered tissues or tissue substitutes can be advantageously employed as primary materials, coatings, covers, cushions, meshes, bags, or liners with certain embodiments of the subject invention. Biological materials can also be employed alongside certain embodiments of the subject invention, for instance, a biological tissue or tissue substitute graft (e.g., Tutoplast Sclera, Pericardium, or Fascia Lata; AMBIO2® Amniotic Membrane; or TARSYS™ bioengineered eyelid spacer graft, all available from Katena, Parsippany, New Jersey) can be placed between the implant and the sclera of the eye to augment or protect the native tissue, or can be placed over the implant to provide a barrier between adjacent tissues and/or a pathway for guided regeneration above, beyond, or adjacent the implant.

Combinations of materials can be advantageously employed in some embodiments (e.g., a strong internal member with a soft outer protective coating or a biocompatible coating). Single material or unitary designs can provide advantages in cost, reduced risk of adverse reaction, manufacturability, robustness, ease of manufacture, and ease of use. Biocompatibility, strength to size ratio, strength to weight ratio, longevity, fracture resistance, cost, availability, and manufacturability can all impact the utility of a given material in certain embodiments.

It is important to the simplified design and function of certain embodiments of the subject invention that the implant have a structural rigidity sufficient to correct and restore the natural curvature and/or axial length of the eye without relying upon complicated insertion or fixation procedures, complicated mechanisms, or excessive tension or deformation within the implant itself. One example of a material suited to application in certain embodiments of the subject invention is titanium, having a long history of biocompatibility, use in surgical implants, high strength to weight ratio, high size to weight ratio, and structural rigidity.

A rigid or high strength material (e.g., titanium or titanium alloy, stainless steel, or other metallic or ceramic materials) can have a high modulus of elasticity (e.g., 105 gigapascals (GPa) to 120 GPa for certain titanium alloys, 113.8 GPa for Ti-6Al-4V ELI (Grade 23), Annealed Titanium Alloy, or 193 GPa for 316 Stainless Steel, annealed bar; with certain other rigid or high strength materials having a modulus of elasticity above, between, or below these exemplary values) and can provide advantages by meeting strength and stiffness requirements to restore the natural curvature and axial length of the eye with a small thickness and reduced weight as compared to semi-rigid or medium strength materials (e.g., a polymer such as Polymethylmethacrylate (PMMA) or other suitable methacrylates or biocompatible polymers can have a modulus of elasticity in the range from 2.4 GPa to 3.4 GPa; with certain other semi-rigid or medium strength materials having a modulus of elasticity above, between, or below these exemplary values) or as compared to flexible, soft, or lower strength materials (e.g., silicone rubber can have a Modulus of Elasticity in a range from 0.00000500 GPa to 1.90 GPa; with certain other flexible, soft, or lower strength materials having a modulus of elasticity above, between, or below these exemplary values.)

Certain embodiments can advantageously fabricate the entire implant of one or more materials having a modulus of elasticity equal to or greater than 105 GPa, alternatively greater than 1.9 GPa, greater than 2 GPa, greater than 2.4 GPa, greater than 3.4 GPa, greater than 4 GPa, greater than 5 GPa, greater than 10 GPa, greater than 20 GPa, greater than 30 GPa, greater than 40 GPa, greater than 50 GPa, greater than 60 GPa, greater than 70 GPa, greater than 80 GPa, greater than 90 GPa, greater than 100 GPa, greater than 110 GPa, greater than 120 GPa, greater than 130 GPa, greater than 140 GPa, greater than 150 GPa, greater than 200 GPa, greater than 250 GPa, greater than 300 GPa, greater than 400 GPa, or greater than 500 GPa (e.g., titanium, titanium alloy, stainless steel, another suitable metal, PMMA, or another biocompatible polymer.)

Certain embodiments can advantageously fabricate the entire implant of one or more materials having a modulus of elasticity equal to or less than 105 GPa, alternatively less than 1.9 GPa, less than 2 GPa, less than 2.4 GPa, less than 3.4 GPa, less than 4 GPa, less than 5 GPa, less than 10 GPa, less than 20 GPa, less than 30 GPa, less than 40 GPa, less than 50 GPa, less than 60 GPa, less than 70 GPa, less than 80 GPa, less than 90 GPa, less than 100 GPa, less than 110 GPa, less than 120 GPa, less than 130 GPa, less than 140 GPa, less than 150 GPa, less than 200 GPa, less than 250 GPa, less than 300 GPa, less than 400 GPa, or less than 500 GPa (e.g., titanium, titanium alloy, stainless steel, another suitable metal, PMMA, siloxanes, silicone, or another biocompatible polymer.)

Certain embodiments can advantageously fabricate the implant of two or more materials (including, e.g., a primary material and a coating) having a difference in modulus of elasticity between the two materials of greater than 1 GPa, alternatively greater than 2 GPa, greater than 3 GPa, greater than 4 GPa, greater than 5 GPa, greater than 6 GPa, greater than 7 GPa, greater than 8 GPa, greater than 9 GPa, greater than 10 GPa, greater than 20 GPa, greater than 30 GPa, greater than 40 GPa, greater than 50 GPa, greater than 60 GPa, greater than 70 GPa, greater than 80 GPa, greater than 90 GPa, greater than 100 GPa, greater than 200 GPa, greater than 300 GPa, greater than 400 GPa, or greater than 500 GPa (e.g., a titanium alloy as a primary material and silicone as a secondary material.) Titanium, when used, can be pure titanium or a titanium alloy, and can be used in a natural state, coated with a titanium oxide, anodized, plated, or otherwise coated. In certain embodiments the base material can be covered, coated, plated, enveloped, or overlaid with a secondary material. Secondary materials and treatments suitable for use in certain embodiments can include silicone, ceramic coatings, and polymer coatings. Secondary materials and surface finishes can range from less than a micrometer thick to providing the majority of the thickness of the finished or coated implant, and can also include bags, meshes, or other coverings place over or around all or part of the implant. A natural, bare, anodized, oxide, or thin coated implant can offer advantages in certain embodiments including ease of manufacture, simplicity, reduced risk of toxicity, and reduced risk of failure. Coated implants can offer advantages to certain embodiments including improved biocompatibility, cushioning, reduced potential for tissue damage, and improved surface texture over the base material.

In certain embodiments the body can have a body width and the plate can have a plate width; the body width being greater than one-half the plate width and the body width being less than the plate width. In certain embodiments the body width can be greater than one-third of the plate width, alternatively greater than two-thirds of the plate width, alternatively greater than three-quarters of the plate width, alternatively greater than 40% of the plate width, alternatively greater than 50% of the plate width, alternatively greater than 60% of the plate width, alternatively greater than 70% of the plate width, alternatively greater than 80% of the plate width, alternatively greater than 90% of the plate width, alternatively greater than 95% of the plate width, alternatively greater than the plate width, or increments of any of the foregoing. In certain embodiments the body width can be less than the plate width, alternatively less than 150% of the plate width, alternatively less than 150% of the plate width, alternatively less than 120% of the plate width, alternatively less than 110% of the plate width, alternatively less than 99% of the plate width, alternatively less than 95% of the plate width, alternatively less than 90% of the plate width, alternatively less than 80% of the plate width, alternatively less than 70% of the plate width, or increments of any of the foregoing.

In certain embodiments the anchor can have an anchor width, the anchor width being greater than the plate width, alternatively greater than 90% of the plate width, alternatively greater than 110% of the plate width, alternatively greater than 120% of the plate width, alternatively greater than 150% of the plate width, alternatively greater than 200% of the plate width, alternatively greater than 250% of the plate width, alternatively greater than 300% of the plate width, alternatively greater than 400% of the plate width, or increments of any of the foregoing. In certain embodiments the anchor width can be less than five times the plate width, alternatively less than four times the plate width, alternatively less than three times the plate width, alternatively less than two times the plate width, alternatively less than 450% of the plate width, alternatively less than 350% of the plate width, alternatively less than 250% of the plate width, alternatively less than 150% of the plate width, alternatively less than 120% of the plate width, alternatively less than 110% of the plate width, or increments of any of the foregoing.

In certain embodiments, the plate can have a plate thickness, the body can have a body thickness, and the anchor can have an anchor thickness; the plate thickness being greater than 50% of the body thickness, the plate thickness being less than 200% of the body thickness, the anchor thickness being greater than 50% of the body thickness, and the anchor thickness being less than 200% of the body thickness, or increments of any of the foregoing.

Alternatively, the plate thickness can be greater than 60% of the body thickness, the plate thickness can be greater than 70% of the body thickness, the plate thickness can be greater than 80% of the body thickness, the plate thickness can be greater than 90% of the body thickness, the plate thickness can be greater than 100% of the body thickness, the plate thickness can be greater than 110% of the body thickness, the plate thickness can be greater than 120% of the body thickness, the plate thickness can be greater than 150% of the body thickness, the plate thickness can be greater than 175% of the body thickness, the plate thickness can be greater than 200% of the body thickness, or increments of any of the foregoing.

Alternatively, the plate thickness can be less than 30% of the body thickness, the plate thickness can be less than 40% of the body thickness, the plate thickness can be less than 50% of the body thickness, the plate thickness can be less than 60% of the body thickness, the plate thickness can be less than 70% of the body thickness, the plate thickness can be less than 80% of the body thickness, the plate thickness can be less than 90% of the body thickness, the plate thickness can be less than 100% of the body thickness, the plate thickness can be less than 110% of the body thickness, the plate thickness can be less than 120% of the body thickness, the plate thickness can be less than 150% of the body thickness, the plate thickness can be less than 175% of the body thickness, the plate thickness can be less than 200% of the body thickness, or increments of any of the foregoing.

Alternatively, the anchor thickness can be greater than 60% of the body thickness, the anchor thickness can be greater than 70% of the body thickness, the anchor thickness can be greater than 80% of the body thickness, the anchor thickness can be greater than 90% of the body thickness, the anchor thickness can be greater than 100% of the body thickness, the anchor thickness can be greater than 110% of the body thickness, the anchor thickness can be greater than 120% of the body thickness, the anchor thickness can be greater than 150% of the body thickness, the anchor thickness can be greater than 175% of the body thickness, the anchor thickness can be greater than 200% of the body thickness, or increments of any of the foregoing.

Alternatively, the anchor thickness can be less than 30% of the body thickness, the anchor thickness can be less than 40% of the body thickness, the anchor thickness can be less than 50% of the body thickness, the anchor thickness can be less than 60% of the body thickness, the anchor thickness can be less than 70% of the body thickness, the anchor thickness can be less than 80% of the body thickness, the anchor thickness can be less than 90% of the body thickness, the anchor thickness can be less than 100% of the body thickness, the anchor thickness can be less than 110% of the body thickness, the anchor thickness can be less than 120% of the body thickness, the anchor thickness can be less than 150% of the body thickness, the anchor thickness can be less than 175% of the body thickness, the anchor thickness can be less than 200% of the body thickness, or increments of any of the foregoing.

In certain embodiments, the plate thickness, the body thickness, and the anchor thickness can each be uniform and about equal. Alternatively, the thickness of the implant can vary from the plate, through the body, to the anchor. The thickness can be smaller at the plate, increasing through the body, and greater at the anchor. The thickness can be greater at the plate, decreasing through the body, and smaller at the anchor.

Alternatively, the plate and anchor can be of uniform thickness, while the body is of greater thickness than either the plate or the anchor. Alternatively, the plate and anchor can be of uniform thickness, while the body is of lesser thickness than either the plate or the anchor.

Alternatively, the plate and body can be of uniform thickness, while the anchor is of greater thickness than either the plate or the body. Alternatively, the plate and body can be of uniform thickness, while the anchor is of lesser thickness than either the plate or the body.

Alternatively, the body and anchor can be of uniform thickness, while the plate is of greater thickness than either the body or the anchor. Alternatively, the body and anchor can be of uniform thickness, while the plate is of lesser thickness than either the body or the anchor.

In certain embodiments, the plate width can be greater than the body width, and the anchor width can be greater than the plate width. Alternatively, the plate width, the body width, and the anchor width can each be uniform and about equal. Alternatively, the width of the implant can vary from the plate, through the body, to the anchor. The width can be smaller at the plate, increasing through the body, and greater at the anchor. The width can be greater at the plate, decreasing through the body, and smaller at the anchor.

Alternatively, the plate and anchor can be of uniform width, while the body is of greater width than either the plate or the anchor. Alternatively, the plate and anchor can be of uniform width, while the body is of lesser width than either the plate or the anchor.

Alternatively, the plate and body can be of uniform width, while the anchor is of greater width than either the plate or the body. Alternatively, the plate and body can be of uniform width, while the anchor is of lesser width than either the plate or the body.

Alternatively, the body and anchor can be of uniform width, while the plate is of greater width than either the body or the anchor. Alternatively, the body and anchor can be of uniform width, while the plate is of lesser width than either the body or the anchor.

In certain embodiments the anchor can include a first anchor point central to the body, a second anchor point medial to the body and either anterior or posterior to the first anchor point, and a third anchor point lateral to the body and either anterior or posterior to the first anchor point.

In certain embodiments the body can include a first anchor point central to the body, and the anchor can include a second anchor point medial to the body and either anterior or posterior to the first anchor point, and a third anchor point lateral to the body and either anterior or posterior to the first anchor point.

In certain embodiments a line drawn from the first anchor point to the second anchor point forms an angle of less than 170 degrees and more than 10 degrees with a line drawn from the first anchor point to the third anchor point.

Alternatively, a line drawn from the first anchor point to the second anchor point can form an angle of less than 160 degrees with a line drawn from the first anchor point to the third anchor point; alternatively, less than 150 degrees; alternatively, less than 140 degrees; alternatively, less than 130 degrees; alternatively, less than 120 degrees; alternatively, less than 110 degrees; alternatively, less than 150 degrees; alternatively, less than 150 degrees; alternatively, less than 100 degrees; alternatively, less than 90 degrees; alternatively, less than 80 degrees; alternatively, less than 70 degrees; alternatively, less than 60 degrees; alternatively, less than 50 degrees; alternatively, less than 40 degrees; alternatively, less than degrees; alternatively, less than 20 degrees, or increments of any of the foregoing.

Alternatively, a line drawn from the first anchor point to the second anchor point can form an angle of more than 160 degrees with a line drawn from the first anchor point to the third anchor point; alternatively, more than 150 degrees; alternatively, more than 140 degrees; alternatively, more than 130 degrees; alternatively, more than 120 degrees; alternatively, more than 110 degrees; alternatively, more than 150 degrees; alternatively, more than 150 degrees; alternatively, more than 100 degrees; alternatively, more than 90 degrees; alternatively, more than 80 degrees; alternatively, more than 70 degrees; alternatively, more than 60 degrees; alternatively, more than 50 degrees; alternatively, more than 40 degrees; alternatively, more than 30 degrees; alternatively, more than 20 degrees, or increments of any of the foregoing.

Alternatively, any of the foregoing lines can be drawn between a feature or point central to the body or the anchor (e.g., a point on the centerline or midpoint of the body or anchor portion of the implant, proximal to or on an edge or boundary along or between the body and the anchor, or at a geometric feature such as the point at which a first arm joins either the body or a second arm) in place of the first anchor point named above.

In certain embodiments the anchor can have a first arm connecting the second anchor point to the body where the first arm can have an arm width less than the body width, and a second arm connecting the third anchor point to the body where the second arm can have an arm width less than the body width. Additionally, or alternatively, the first arm can have a first arm length less than the body length and the second arm can have a second arm length less than the body length.

In certain embodiments the first arm and the second arm form a Y shape with respect to the body. Alternatively, the first arm and the second arm can form a T shape with respect to the body. Alternatively, the first arm and the second arm can form a U shape with respect to the body. Alternatively, the first arm and the second arm can form an inverted Y, inverted U, an "arch" shape, or "arrow" shape with respect to the body. Alternatively, the first arm and the second arm can form a Y shape or an arrow shape that is symmetric with respect to the body. Alternatively, the first arm and the second arm can form a Y shape or an arrow shape that is asymmetric with respect to the body. Alternatively, the first arm and the second arm can form a Y shape or an arrow shape that is irregular with respect to the body.

In certain embodiments the plate can have a first radius of curvature (RP), the anchor can have a second radius of curvature (RA), the first radius of curvature being less than the second radius of curvature (RP<RA). Alternatively, the first radius of curvature can be greater than the second radius of curvature (RP>RA).

In certain embodiments the body can have a first radius of curvature (RB1) proximate the plate, the body can have a second radius of curvature (RB2) proximate the anchor, the first radius of curvature being less than the second radius of curvature (RB1<RB2). Alternatively, the first radius of curvature can be greater than the second radius of curvature (RB1>RB2). The surface connecting RB1 to RB2 can be tangent, continuous but incongruent, or discontinuous. RB1 can be equal to RP, alternatively RB1 can be greater than RP, alternatively RB1 can be less than RP. The surface connecting RB1 to RP can be tangent, continuous but incongruent, or discontinuous. RB2 can be equal to RA, alternatively RB2 can be greater than RA, alternatively RB2 can be less than RA. The surface connecting RB2 to RA can be tangent, continuous but incongruent, or discontinuous.

Each of the above relationships can be selected to offer a benefit in cost, manufacturability, or clinical efficacy (e.g., an incongruent surface connecting RB1 to RB2 can be less costly to manufacture; or a tangent surface connecting RB1 to RP can produce improved clinical outcomes in restoration of natural curvature.)

In certain embodiments the connection between the plate and the body can be continuous and smooth at the concave scleral mating surface. Additionally, or alternatively, the connection between the body and the anchor can be continuous and smooth at the concave scleral mating surface. Additionally, or alternatively, the body can have a stepwise transition of curvature that maintains surface tangency between the first radius of curvature (RB1) and the second radius of curvature (RB2). Additionally, or alternatively, the body can have a third radius of curvature (RB3) that is different than RB1 and RB2 (e.g., RB3 can be more than twice RB2.) Additionally, or alternatively, the body can have a region of neutral (neither concave nor convex) curvature, a flat region, a piecewise linear region, or a concave region.

One embodiment of the subject invention provides a unitary rigid ophthalmic surgical implant for improving vision in a patient by restoring the natural curvature and natural axial length of an eye; the implant having a plate with a concave scleral mating surface configured to restore the natural curvature of a posterior portion of the eye, an anchor with a concave scleral mating surface configured to approximate the natural curvature of an anterior portion of the eye, and a body with a continuous and smooth concave scleral mating surface connecting the plate to the anchor. The eye having a natural axial length and the implant can have a total implant length less than the natural axial length of the eye. The body can have a body width and the plate having a plate width; the body width being less than the plate width. The anchor can have an anchor width greater than the plate width. The plate having a plate thickness; the body having a body thickness; the anchor having an anchor thickness; the plate thickness, the body thickness, and the anchor thickness each being about equal.

Certain embodiments can further provide a first anchor point central to the body, a second anchor point medial or lateral to the body and either anterior or posterior to the first anchor point, and a third anchor point lateral to the body and either anterior or posterior to the first anchor point; wherein a line drawn from the first anchor point to the second anchor point forms an angle of less than 170 degrees and more than 10 degrees with a line drawn from the first anchor point to the third anchor point.

Certain embodiments can further provide a first arm connecting the second anchor point to the body where the first arm can have an arm width less than the body width, and a second arm connecting the third anchor point to the body where the second arm can have an arm width less than the body width. The first arm can have a first arm length less than the body length and the second arm can have a second arm length less than the body length. The first arm and the second arm can form a Y shape that is symmetric with respect to the body.

In certain embodiments the plate can have a constant radius of curvature (R) (e.g., a single value for radius of curvature from a plate, through a body, and to an anchor.) The value of R in millimeters (mm) can be equal to the value of an anchor width (AW) in mm (e.g., R=AW), alternatively R can be less than 99% of AW, less than 95% of AW, less than 90% of AW, less than 85% of AW, less than 80% of AW, less than 75% of AW, less than 70% of AW, less than 65% of AW, less than 60% of AW, less than 55% of AW, less than 50% of AW, less than 45% of AW, less than 40% of AW, or any fraction of the foregoing. Alternatively, R can be more than AW, more than 105% of AW, more than 110% of AW, more than 115% of AW, more than 120% of AW, more than 125% of AW, more than 130% of AW, more than 135% of AW, more than 140% of AW, more than 145% of AW, more than 150% of AW, more than 175% of AW, more than 200% of AW, or any fraction of the foregoing.

In certain embodiments, the value of R in millimeters (mm) can be equal to the value of a body width (BW) in mm (e.g., R=BW), alternatively R can be less than 99% of BW, less than 95% of BW, less than 90% of BW, less than 85% of BW, less than 80% of BW, less than 75% of BW, less than 70% of BW, less than 65% of BW, less than 60% of BW, less than 55% of BW, less than 50% of BW, less than 45% of BW, less than 40% of BW, or any fraction of the foregoing. Alternatively, R can be more than BW, more than 105% of BW, more than 110% of BW, more than 115% of BW, more than 120% of BW, more than 125% of BW, more than 130% of BW, more than 135% of BW, more than 140% of BW, more than 145% of BW, more than 150% of BW, more than 175% of BW, more than 200% of BW, or any fraction of the foregoing.

In certain embodiments, the value of R in millimeters (mm) can be equal to the value of a plate width (PW) in mm (e.g., R=PW), alternatively R can be less than 99% of PW, less than 95% of PW, less than 90% of PW, less than 85% of PW, less than 80% of PW, less than 75% of PW, less than 70% of PW, less than 65% of PW, less than 60% of PW, less than 55% of PW, less than 50% of PW, less than 45% of PW, less than 40% of PW, or any fraction of the foregoing. Alternatively, R can be more than PW, more than 105% of PW, more than 110% of PW, more than 115% of PW, more than 120% of PW, more than 125% of PW, more than 130% of PW, more than 135% of PW, more than 140% of PW, more than 145% of PW, more than 150% of PW, more than 175% of PW, more than 200% of PW, or any fraction of the foregoing.

In certain embodiments the plate can have a first radius of curvature (RP), the anchor can have a second radius of curvature (RA), the first radius of curvature being less than the second radius of curvature (RP<RA). The body can have a first radius of curvature (RB1) proximate the plate, the body can have a second radius of curvature (RB2) proximate the anchor, the first radius of curvature being less than the second radius of curvature (RB1<RB2); the connection between the plate and the body being continuous and smooth at the concave scleral mating surface; the connection between the body and the anchor being continuous and smooth at the concave scleral mating surface; and the body can have a stepwise transition of curvature that maintains surface tangency between the first radius of curvature (RB1) and the second radius of curvature (RB2).

In certain embodiments the plate can provide one or more attachments points (e.g., for the optional purpose that the surgeon, if greater indentation of the eye is desired, will have the option of suturing a local sponge (such as those readily available for common retinal detachment repair) or other addition on the plate.) Attachment points can take the form of one or more holes, slots, protrusions, or other features known in the art to encourage or enhance the retention of suture. One embodiment provides two holes symmetrically located proximal the center of the plate, the holes spaced and sized to facilitate passage of suture.

One embodiment of the subject invention provides a method of surgery for improving vision in a patient by restoring, supporting, or helping to preserve the natural curvature and natural axial length of an eye, the eye having a conjunctiva and a sclera; the method of surgery including the steps of providing a unitary rigid ophthalmic surgical implant in accordance with the subject invention, selecting a quadrant of the eye, dissecting the conjunctiva to expose the sclera in the selected quadrant, inserting the implant, plate first and with the concave scleral mating surface in intimate contact with the scleral surface beneath the conjunctiva in the selected quadrant, advancing the implant until the anchor is 3 mm to 10 mm behind the limbus, fixing the body of the implant to the sclera, determining a desired position of the implant to restore the natural curvature and natural axial length of the eye, and anchoring the anchor to the sclera in the desired position in at the least two anchor points to restore the natural curvature and natural axial length of the eye.

In one embodiment the selected quadrant can be either the inferotemporal or superotemporal quadrant. The method additionally or alternatively can include the step of attaching an autograft, allograft, xenograft, or synthetic scleral graft to the sclera beneath the implant, either before or after placing the implant.

The step of determining a desired position of the implant can include measuring the corrected AP length and adjusting the position of the implant intraoperatively. Additionally, or alternatively, the step of determining a desired position of the implant can include referring to a nomogram or preoperative measurement and adjusting the position of the implant intraoperatively.

Ultrasound can measure how long the eye is, and how much deviated from the normal 22 mm to 24 mm length. Ultrasound can also show the deformity and shape of the back of the eye. There are also other means of measuring the length of the eye more precisely (e.g., with a laser beam using an IOL Master 500 (Carl Zeiss Meditec AG, Jena, Germany) or Lenstar LS900 (Haag Steit AG, Koeniz, Switzerland) commonly used to measure the length of the eye prior to a cataract surgery) to calculate the intraocular lens power for the lens to be placed. Intraocular devices such as an Optiwave Refractive Analysis (ORA) or a simple autorefractometer can be used in certain embodiments of the present invention to determine the refractive error of the eye just when the implant is placed in the eye during the surgery to make sure the implant is fixated at the correct position to provide the desired length and/or curvature of the eye. The desired length will be the length that results in minimal or no refractive error after the placement in the case where an implant is placed to correct a refractive error. In some cases, the desired length would be about 22-24 mm if an implant is placed to inhibit stretching of the back of the eye to prevent, inhibit, reduce, or correct the macular pathology, namely macular schisis, myopic macular hole, macular scarring, and related pathologies.

Certain embodiments can additionally or alternatively include the step of closing the conjunctiva over the implant and the step of attaching an autograft, allograft, xenograft, or synthetic scleral graft beneath, around, and/or over the implant. The step of dissecting the conjunctiva can include a blunt backwards dissection that opens a nested pocket for the implant between the conjunctiva and the sclera.

One embodiment of the subject invention provides a surgical implant for changing the axial length of an eye, having a body with a lower surface for facing a scleral surface of the eye and an upper surface, a macular indenter extending from a posterior end of the body, one or more anchor arms extending from an anterior end of the body, opposite the posterior end of the body, and one or more anchor portals, each passing through the body at a point on or adjacent an anchor arm, wherein the lower surface has a compound concavity defined by a first radius of curvature at the posterior end of the body and a second radius of curvature at the anterior end of the body, the first radius of curvature being smaller than the second radius of curvature. In certain embodiments the first radius of curvature extends along the lower surface through the macular indenter, the second radius of curvature extends along the lower surface through the one or more anchor arms, and the first radius of curvature meets the second radius of curvature in a tangency along the bottom surface at a point between the posterior end of the body and the anterior end of the body. In certain embodiments the macular indenter extends from the lower surface of the body to the upper surface of the body and is generally cylindrical in shape, defining a cylindrical central axis normal to the lower surface at the centroid of the macular indenter. In certain embodiments the body can have a longitudinal central axis running from along a midplane of the body from the posterior end to the anchor end, wherein two anchor arms of equal length and equal width form a symmetric anchor structure with symmetry about a plane passing through the longitudinal central axis of the body and the cylindrical central axis of the macular indenter. The body can have a generally consistent body width and body thickness between the macular end and at least one of the anchor arms can have an arm width less than the body width and an arm thickness about equal to the body thickness.

One embodiment of the subject invention provides a surgical implant for changing the axial length of an eye having a plate, an anchor, an elongate body having a body length extending between the anchor and the plate, a concave scleral surface connecting the plate, the body, and the anchor, a convex orbital surface opposite the scleral surface; and a pair of opposing lateral sides connecting the orbital surface and the scleral surface along at least a portion of the body length The plate can have a shape that defines a plate width at the scleral surface, the elongate body can have a shape that defines a body width between opposing lateral sides at the scleral surface, the anchor can have two suture portals extending from the scleral surface to the orbital surface and defining an anchor width therebetween, wherein the body width is at least about ⅔ of the plate width and the anchor width is greater than the body width.

In certain embodiments the plate has a center of mass, the body has a center of mass, a length vector is defined as extending from the plate center of mass through the body center of mass, and the anchor comprises two anchor arms, the first anchor arm extending from the body to a suture portal along a path at a first angle to the length vector, the second anchor arm extending from the body to a suture portal along a path at a second angle to the length vector, the two arms defining a space therebetween, wherein the first angle and the second angle are on opposite sides of the length vector and the first angle and the second angle are of equal magnitude.

In certain embodiments the first arm has a first length and the second arm has a second length, the second length being equal to the first length.

One embodiment of the subject invention provides a surgical implant for changing the axial length of an eye having a concave scleral facing surface extending from a posterior end of the implant to an anterior end of the implant and defining an anterior-posterior (AP) direction along the implant, the scleral surface can have a posterior radius of curvature in a region proximate the posterior end, and an anterior radius of curvature in a region proximate the anterior end, the posterior radius being smaller than the anterior radius. This embodiment further provides a concave macular indenter plate at the posterior end of the implant, having a radius of curvature essentially the same as the posterior radius and a plate width measured across the scleral surface and normal to the AP direction; and a concave anchor at the anterior end of the implant, having a radius of curvature essentially the same as the anterior radius and an anchor width measured across the scleral surface and normal to the AP direction. This embodiment further provides a concave body portion connecting the plate and the anchor, having a variable radius of curvature that changes from essentially the same as the posterior radius in a region proximate the plate to essentially the same as the anterior radius in a region proximate the anchor, wherein the variable radius of curvature of the body maintains continuity of curvature from a region proximate the plate to a region proximate the anchor, wherein the body comprises two regions of constant radius of curvature, the two regions being mutually tangent at their point of intersection. Alternatively, the body comprises a region of constant rate of change in the radius of curvature between the anterior radius and the posterior radius.

One embodiment of the subject invention provides a surgical implant for changing the axial length of an eye having a plate located at a posterior end of the implant, an anchor located at an anterior end of the implant, an elongate body having a body length extending between the anchor and the plate, a concave scleral surface extending from the posterior end of the implant to the anterior end of the implant, connecting the plate, the body, and the anchor, and defining an anterior-posterior (AP) direction along the implant, a convex orbital surface opposite the scleral surface, and a pair of opposing lateral sides connecting the orbital surface and the scleral surface along at least a portion of the body length; wherein the plate has a shape that defines a plate width at the scleral surface, the elongate body has a shape that defines a body width between opposing lateral sides at the scleral surface, the anchor comprises two suture portals extending from the scleral surface to the orbital surface and defining an anchor width therebetween, the body width is at least about ⅔ of the plate width, and the anchor width is greater than the body width. Additionally, the implant can include a concave scleral facing surface having a posterior radius of curvature in a region proximate the posterior end, and an anterior radius of curvature in a region proximate the anterior end, the posterior radius being smaller than the anterior radius; a concave macular indenter plate at the posterior end of the implant, having a radius of curvature essentially the same as the posterior radius and a plate width measured across the scleral surface and normal to the AP direction; a concave anchor at the anterior end of the implant, having a radius of curvature essentially the same as the anterior radius and an anchor width measured across the scleral surface and normal to the AP direction; a concave body portion connecting the plate and the anchor, having a variable radius of curvature that changes from essentially the same as the posterior radius in a region proximate the plate to essentially the same as the anterior radius in a region proximate the anchor.

One embodiment of the subject invention provides a surgical implant (100) for changing the axial length of an eye, having a plate (110) located at a posterior end of the implant, an anchor (130) located at an anterior end of the implant, an elongate body (120), the body can have a body length extending between the anchor and the plate, a concave scleral surface (140) extending from the posterior end of the implant to the anterior end of the implant, connecting the plate, the body, and the anchor, a convex orbital surface (150) opposite the scleral surface, and a pair of opposing lateral sides (160) connecting the orbital surface and the scleral surface along at least a portion of the body length; wherein the scleral surface can have a posterior radius of curvature (R1) in a region proximate the posterior end, and an anterior radius of curvature (R2) in a region proximate the anterior end, the posterior radius being smaller than the anterior radius, the plate can have a shape that defines a plate width (PW) at the scleral surface; the elongate body can have a shape that defines a body width (BW) between opposing lateral sides at the scleral surface, the anchor can have two suture portals (131A, 131B) extending from the scleral surface to the orbital surface and defining an anchor width (AW) therebetween, the body width being at least about ⅔ of the plate width and the anchor width being greater than the body width.

Additionally, certain embodiments can provide a concave macular indenter plate at the posterior end of the implant having a radius of curvature essentially the same as the posterior radius and a plate width measured across the scleral surface and normal to the AP direction, a concave anchor at the anterior end of the implant having a radius of curvature essentially the same as the anterior radius and an anchor width measured across the scleral surface and normal to the AP direction, a concave body portion connecting the plate and the anchor having a variable radius of curvature that changes from essentially the same as the posterior radius in a region proximate the plate to essentially the same as the anterior radius in a region proximate the anchor.

FIG. 1 is a three-dimensional representation of one embodiment providing a unitary rigid ophthalmic surgical implant for improving vision in a patient by restoring the natural curvature and natural axial length of an eye in accordance with the subject invention. The implant 100 includes a plate 110 located at a posterior end of the implant, an anchor 130 located at an anterior end of the implant, an elongate body 120, the body having a body length extending between the anchor and the plate. The implant has two distinct curvatures, a larger anterior radius of curvature transitions in a smooth tangent surface junction at 121. A concave scleral surface 140 extends from the posterior end of the implant to the anterior end of the implant, connecting the plate, the body, and the anchor. A convex orbital surface 150 is seen opposite the scleral surface, and a pair of opposing lateral sides 160 connect the orbital surface and the scleral surface along at least a portion of the body length. The anchor having two anchor points in the form of suture portals 131A, 131B extending from the scleral surface to the orbital surface at the end of two anchor arms, 132A and 132B, respectively. A third anchor point in the form of suture portal 131C extends from the scleral surface to the orbital surface within the anchor, proximate and central to the body.

Figure 2:
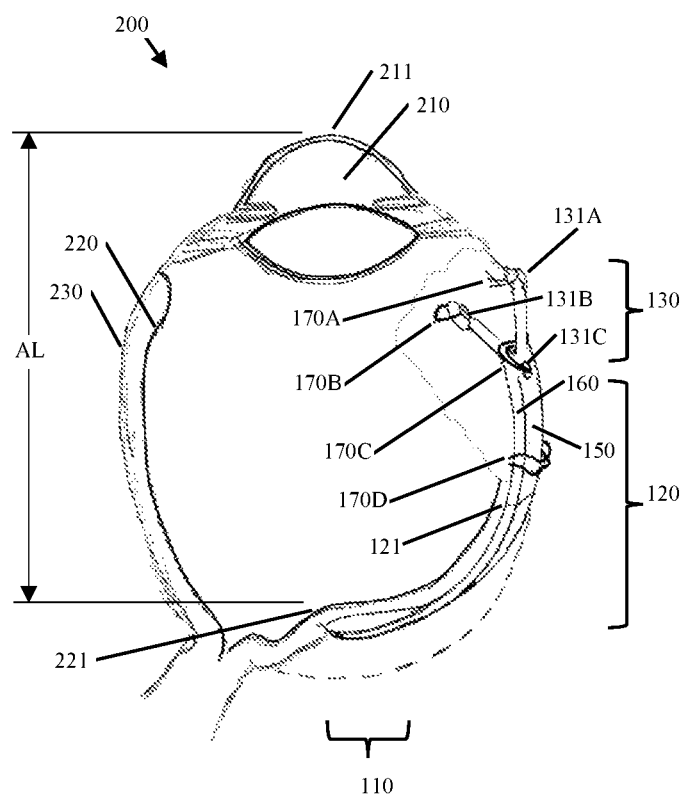
FIG. 2 shows a three-dimensional representation of an eye treated with one embodiment of an implant restoring the natural curvature and natural axial length of the eye in accordance with the subject invention.

FIG. 2 shows a three-dimensional representation of an eye 200 treated with one embodiment of an implant restoring the natural curvature and natural axial length AL of the eye through a surgical technique in accordance with one embodiment of the subject invention. The axial length AL of the eye is measured from the anterior surface 211 of the cornea 210 to the restored axial location 221 of a point on the retina 220 just above the plate 110, where the plate supports the retina 220 and sclera 230. The conjunctiva, just outside of the sclera 230, is not shown in this view. Sutures 170A, 170B, 170C, 170D hold the body 120 of the implant and fasten anchor points 131A, 131B, and 131C, respectively, to the sclera. Suture 170D forms an initial fixation by wrapping loosely around the body 120 while still allowing for axial adjustment of the implant to restore vision in the patient prior to fixation of sutures 170A, 170B, and 170C to fasten anchor points 131A, 131B, and 131C, respectively, to the sclera. The implant has two distinct curvatures, a larger anterior radius of curvature transitions in a smooth tangent surface junction at 121.

Figure 3A:
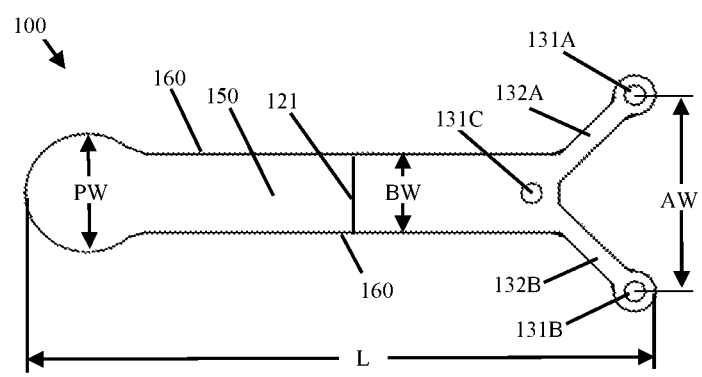
FIGS. 3A-3B show a top view (FIG. 3A) and a side view (FIG. 3B) of one embodiment of an implant in accordance with the subject invention.
Figure 3B:
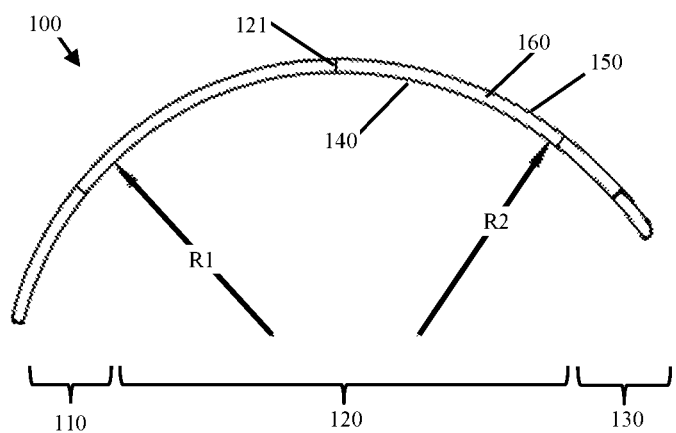

FIGS. 3A and 3B contain a top view and a side view, respectively, of one embodiment of a unitary rigid ophthalmic surgical implant for improving vision in a patient by restoring the natural curvature and natural axial length of an eye in accordance with the subject invention. The implant 100 includes a plate 110 located at a posterior end of the implant, an anchor 130 located at an anterior end of the implant, an elongate body 120, the body having a body length extending between the anchor and the plate. A concave scleral surface 140 extends from the posterior end of the implant to the anterior end of the implant, connecting the plate, the body, and the anchor. A convex orbital surface 150 is seen opposite the scleral surface, and a pair of opposing lateral sides 160 connect the orbital surface and the scleral surface along at least a portion of the body length. The scleral surface has a posterior radius of curvature R1 in a region proximate the posterior end, and an anterior radius of curvature R2 in a region proximate the anterior end, the posterior radius being smaller than the anterior radius. The plate has a shape that defines a plate width PW at the scleral surface. The elongate body has a shape that defines a body width BW between opposing lateral sides at the scleral surface. The anchor has two anchor points 131A and 131B, respectively, extending from the scleral surface to the orbital surface and defining an anchor width AW spanned by two anchor arms 132A and 132B, respectively. A third anchor point 131C extends from the scleral surface to the orbital surface within the anchor but proximate and central to the body. In this embodiment the body width BW is at least about ⅔ of the plate width PW and the anchor width AW is greater than the body width BW.

Figure 4:
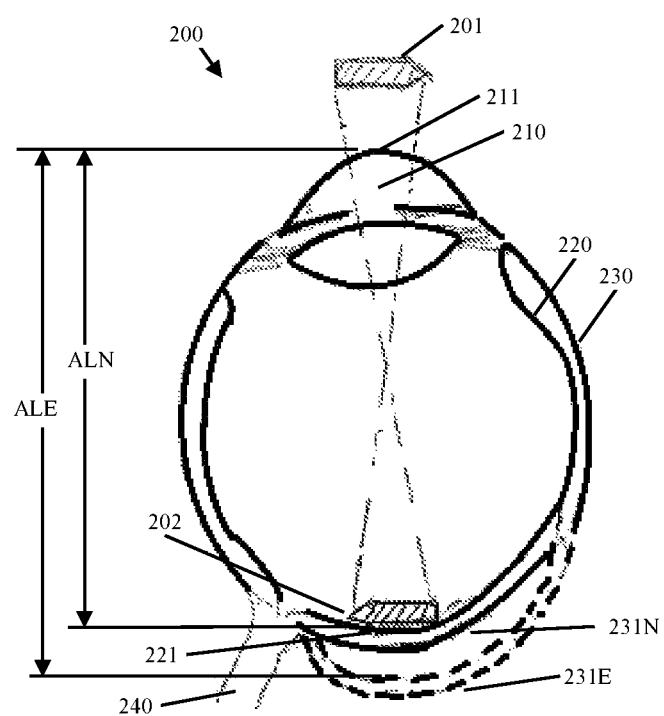
FIG. 4 shows an eye with normal shape and normal refraction and an elongated eye representing myopia due to axial lengthening of the eye, as can be treated by the implants and methods of the subject invention.

FIG. 4 shows an eye 200 with normal eye shape 231N and normal refraction to focus the image 202 of the object 201 on the retina 220 and an elongated eye shape 231E representing myopia and failure to focus the image 202 on the retina 220. In some embodiments, the normal axial length ALN of the eye and the elongated axial length ALE of the eye are each measured from the anterior surface 211 of the cornea 210 to a focal point on the macula 221. The optic nerve is 240. The retina 220 is an inner lining of neural tissue. When the image forms on the retina in a normal length eye, it can be properly focused on the retina. The image can fall in front of the retina when the eye is myopic.

Figure 5:
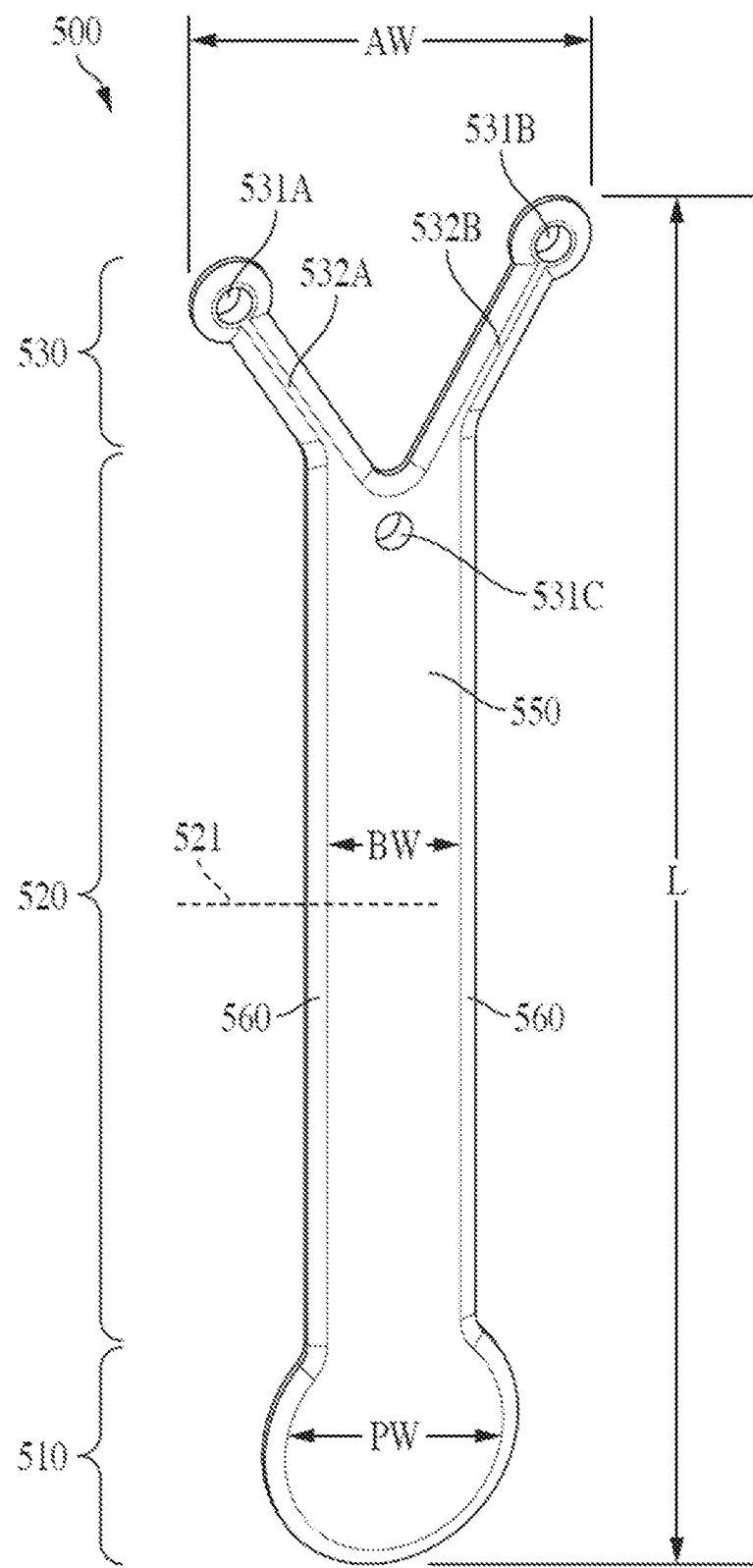
FIG. 5 shows a top perspective view of one embodiment of an implant in accordance with the subject invention.

FIG. 5 contains an engineering sketch defining a top (at a slight perspective) view of one exemplary embodiment of a manufacturing intermediate (e.g., sheet metal flat stamped blank, prior to bending) useful in producing a unitary rigid ophthalmic surgical implant for improving vision in a patient by restoring the natural curvature and natural axial length of an eye in accordance with the subject invention. The blank 500 includes a "spoon" or plate 510 located at a posterior end of the implant, an anchor 530 located at an anterior end of the implant, an elongate body 520, the body having a body length extending between the anchor and the plate. The plate, the body, and the anchor producing a linear implant length, L (30.5 mm), measured from a posterior edge of the plate to an anterior edge of the anchor. A flat surface that can later be bent to form a concave scleral surface (not visible, behind the implant in this view) extends from the posterior end of the implant to the anterior end of the implant, connecting the plate, the body, and the anchor. A flat surface 550 that can later be bent to form a convex orbital surface is visible, and a pair of opposing lateral sides 560 connect the orbital surface and the scleral surface along at least a portion of the body length. The flat surface is denoted for bending to form a scleral surface having a posterior radius of curvature R1 (or diameter=25 mm) in a region proximate the posterior end, and an anterior radius of curvature R2 (or diameter=29 mm) in a region proximate the anterior end, the posterior radius being smaller than the anterior radius. A bending axis 521 marks the intended transition from anterior radius to posterior radius in the finished implant located 16.50 mm from the posterior end and 14.00 mm from the anterior end of the implant. The plate has a shape that defines a plate width PW at the scleral surface and/or at the orbital surface, respectively. The elongate body has a shape that defines a body width BW between opposing lateral sides at the scleral surface. The anchor has two anchor points 531A and 531B, respectively, extending from the scleral surface to the orbital surface and defining an anchor width AW spanned by two anchor arms 532A and 532B, respectively. A third anchor point 531C extends from the scleral surface to the orbital surface within the anchor but proximate and central to the body. In this embodiment the body width BW is at least about ⅔ of the plate width PW and the anchor width AW is greater than the body width BW. Notes indicate the anchor arms are to be of a width (e.g., 1 mm) less than the diameter of their respective anchor points and less than one half the width of the body (BW), the plate is to be 0.5 mm thick, the body, arms, and anchor points can have rounded edges that are curved to flat, or alternatively, sharp or square. Cross sectional sketches detail exemplary geometry, rounds, and edge treatments of the body, the spoon or plate, and the short arms of the anchor.

In certain embodiments, the transition from body to anchor is defined at a point of transition from a body width or thickness to an anchor width or thickness. This point of transition can be defined by a change in width or thickness of the implant, or by the beginning of a gradual increase in width or thickness of the implant, or at a specified distance (e.g., 1 mm or 0.5 mm) from such a point. Alternatively, the anchor can be defined as the point of origin of one or more anchor arms protruding from the body. Alternatively, the anchor can be defined by the position of one or more anchor points (e.g., 531C) or at a specified distance, radius, or diameter (e.g., 1 mm or 0.5 mm) away from a center, edge, or quadrant of one or more anchor points in a specified direction.

Figure 6A:
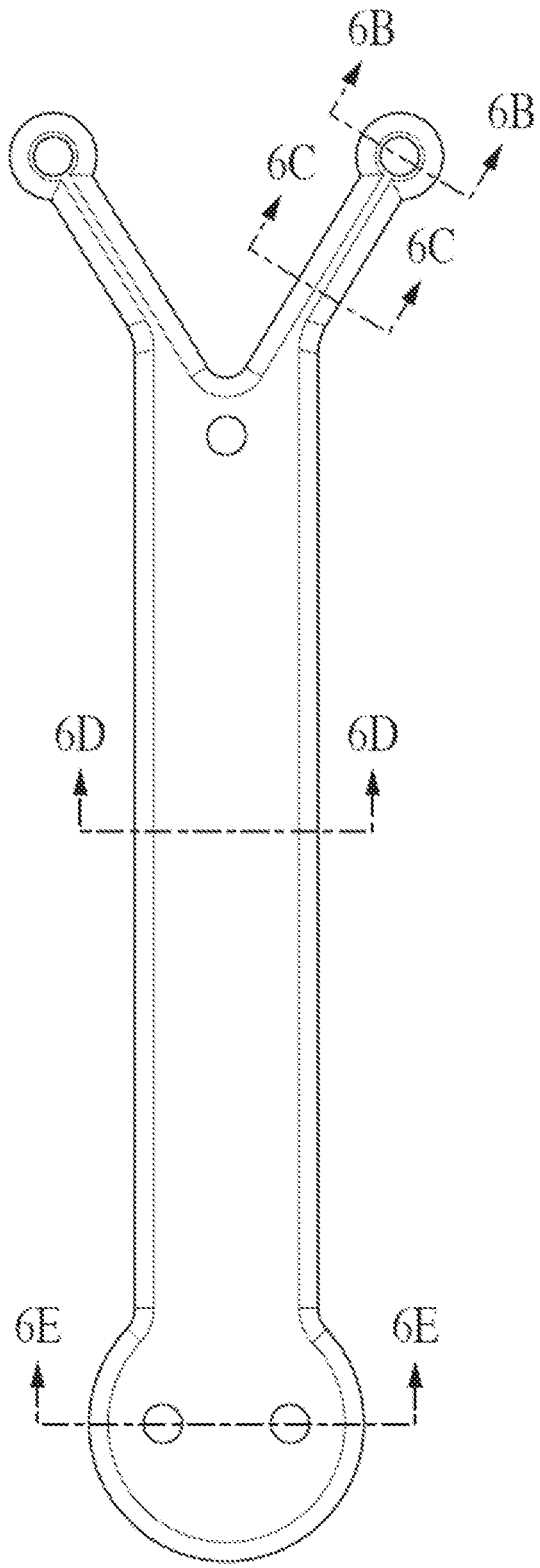
FIGS. 6A-6E show a top view, an end view, and four section views of one embodiment of an implant in accordance with the subject invention.
Figure 6B:
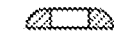
Figure 6C:
Figure 6D:
Figure 6E:

FIGS. 6A-6E show a top view, end view, and section views of one embodiment of an implant in accordance with the subject invention. FIG. 6A shows top and end views of an embodiment of an implant with rounded top edges, three anchor points, and two additional suture holes in the plate (e.g., useful for attaching a sponge or other item.) FIG. 6B shows a cross section through one of the anchor points. An anchor hole (e.g., 1 mm diameter through hole) is supported around the hole diameter by a wall (e.g., 0.5 mm thick) with rounded outer and upper edges (e.g., a full or partial corner round on the edge around all or part of the hole.) FIG. 6C shows a cross section of an anchor arm having a rounded or partially rounded top profile and a flat bottom. FIG. 6D shows a cross-sectional profile of a flat body with rounded upper corner edges. FIG. 6E shows a cross section through the plate with two additional suture holes.

Figure 7:
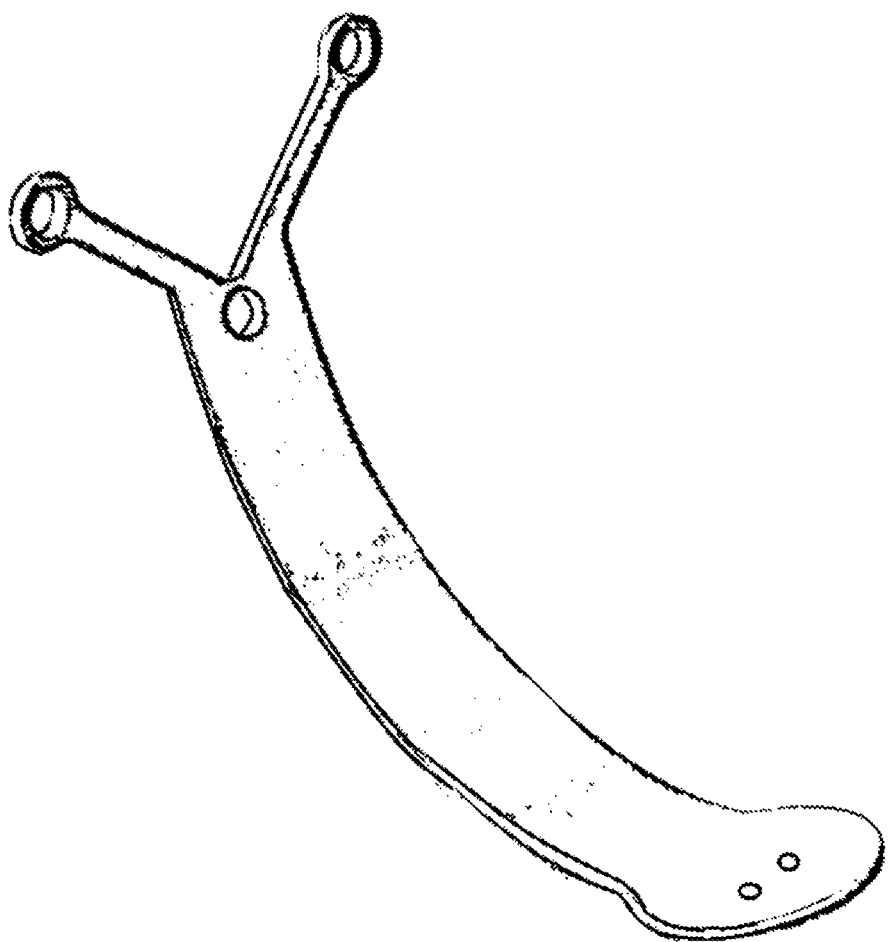
FIG. 7 shows a perspective line drawing of one embodiment of an implant in accordance with the subject invention.

FIG. 7 shows a perspective line drawing of one embodiment of an implant in accordance with the subject invention. The curvature and three-dimensional shape of this embodiment is visible, curving from an anchor portion with three attachment points through a body to a plate portion with two additional optional holes or attachment points.

Certain embodiments of the subject invention provide for improved stability of the implant following surgical placement. The quantity, location, orientation, design, placement, and configuration of attachment points can influence implant stability, which can influence patient outcomes. Sutures are one form of fixation. Non-absorbable sutures can be used for a secure and lasting fixation of the implant. Absorbable sutures can be employed to secure an implant in place until sufficient healing and formation of scar tissue has occurred to hold the implant in place before the sutures are absorbed. Multiple attachment points can be provided. In some embodiments two attachment points are provided at an anterior end of the implant, separated by an anchor distance measured across the body of the implant in a mediolateral direction. Attachment points at the anterior end of the implant can provide benefits in ease of access and attachment. Attachment points spread further apart from each other and from the body of the implant and/or located along an edge or periphery of the implant can provide improved leverage, stability, and holding power. Attachment points in the central or posterior regions of the implant can provide advantageous leverage or fixation by their proximity to the plate. Attachment points placed closer to each other, closer to the body, or closer to the plate can provide advantages of avoiding ocular muscle, nerve, and vascular attachments and providing better access and more options for attachment (e.g., by suturing across two or more anchor points with the same suture and/or passing multiple sutures through one or more attachment points.)

Some embodiments of the subject invention provide means to achieve a desired AP length, shortening, or reshaping of the elongated eye. Experience of the surgeon (e.g., by tracking of results across multiple patients and/or multiple surgeries), improved nomograms, or intraocular AP length measurements can all contribute to improved outcomes. The subject invention provides means to avoid unexpected damage (e.g., breaking of a vessel despite the blunt dissection.) The surgical approach is optimized to minimize risk, and the implant is specifically sized to fit between anatomical landmarks of the eye. In certain embodiments erosion over the implant is minimized by placing a biologic augmentation graft (e.g., TUTOPLAST®) in proximity to the implant. The concave scleral mating surface of the implant can be designed to remain in intimate contact with the scleral surface beneath the conjunctiva with or without application of a biologic augmentation or other graft.

In certain embodiments the procedure will normalize only about a 5 mm diameter section of the back of the eye where the plate is sitting. Advantageously, this can be the most important 5 mm section of the eye. Serious complications can happen here if the eye is too long. Pulling the center 5 mm will provide refractive correction for the eye. Under extremely rare conditions, an implantation site can get infected and implant removal can be required. The subject invention provides the possibility of easy removal in the case of infection or post-surgical complications. The wide width of the body close to the size of the plate will allow easy retrieval if the implant needs to be removed by minimizing adherence of the scar tissue that later forms around the body increasing difficulty of removal. Therefore, selection of a body width and/or height close to that of the plate provides advantages to the surgeon and to the patient.

Pre-existing scarring of the sclera where the placement of the implant is intended to pass or attach can be present with previous scleral implant surgery or with severe previous eye traumas. The implants and methods of the subject invention minimize the effects of scar tissue on the surgical procedure by providing in certain embodiments an implant with a uniform or tapered thickness, small changes in width, and an implant length which is less than the axial length of the eye. The subject invention facilitates a broad range of surgical approaches that can be done with a surgical microscope, magnifying loops, or with the naked eye depending on surgeon preference.

In accordance with the methods of certain embodiments of the subject invention, the axial length of the eyeball can be measured (e.g., in the office, days or weeks prior to the surgery.) Based on the axial length, the desired size implant can be chosen. Certain embodiments of the present invention offer the advantages of a standard procedure with iterations of implant parameters and design features to account for the unique situation of each patient. Implants in accordance with certain embodiments of the present invention can be offered in kits, advantageously providing surgeons with an array of options at varying implant lengths, widths, thicknesses, curvatures, anchor configurations, materials, coatings, and accessory combinations. For example, a kit can include three implants, each having a common 5 mm diameter circular plate, anchor width of 10 mm, body width of 4 mm, and anterior radius of 14.5 mm with each of the three implants having a unique posterior radius of 12.0 mm, 12.5 mm, and 13.0 mm, respectively. As can be appreciated, other variables can be varied or held constant within a kit or across different kits and this can result in multiple kit configurations of different sizes, each offering advantages to the surgeon in terms of cost, availability, or ease of use.

The surgical instruments required to practice the subject invention are in certain embodiments very simple. Instruments include but are not necessarily limited to sharp scissors for cutting the conjunctiva, forceps to hold the implant and conjunctiva and the sclera, calipers to measure surgical distances, a couple of needle holders, and sutures. In certain embodiments the subject invention provides for precision intraoperative AP length measurement or intraoperative refractive power (e.g., using an OCULAR RESPONSE ANALYZER® (ORA) device, Reichert, Inc., Depew, NY) to achieve the desired restoration of length and natural curvature of the eye.

Restoration can be complete or partial, lengthening or shortening or reshaping as needed to restore vision to a patient. Axial length is a linear length measurement and can be measured in a straight line or along a vector or measurement axis (e.g., using ultrasound or optical measurement instruments) from an anterior surface of the cornea or other suitable anatomic landmark to a point of restoration on the concave inner retinal surface (e.g., measurements can be taken of uncorrected actual pre-surgical length and/or curvature; natural, proper-functioning, or desired length and/or curvature; and/or corrected actual, improved-functioning, or post-surgical condition.)

In some embodiments total linear implant length can be measured in a straight line or along a vector from a posterior extent of an implant to an anterior extent of an implant and in certain embodiments this will result in total implant length being measured from a posterior end or extent of a plate to an anterior end or extent of an anchor. Linear widths, thicknesses, or lengths can be a maximum, a minimum, or a local measurement (e.g., the maximum or minimum length, width, or height measurable at any point along the implant or the maximum or minimum length, width, or height measurable within a specified region, portion, feature or area of the implant; e.g., overall implant length, width of an anchor arm, body thickness, or plate diameter), and can be categorized as any of constant or variable, continuous or discontinuous, piecewise linear, curvilinear, rectilinear, actual or approximate, across, around, through, or over a section, region, feature, or area of the implant. Linear measurements can include the straight-line measurement of the minimum distance between two points in space. Unless otherwise specified, measurements discussed herein refer to linear measurements.

Alternatively, in some embodiments an arcuate implant length can be measured in a along a curve, path, or arc from posterior extent of an implant to an anterior extent of an implant and in certain embodiments this will result in total arcuate implant length being measured from a posterior end or extent of a plate to an anterior end or extent of an anchor along a surface (e.g., the scleral mating surface of an implant.) Arcuate widths, thicknesses, or lengths can be a maximum, a minimum, or a local measurement (e.g., the maximum or minimum arcuate length, width, or height measurable at any point along the implant or the maximum or minimum arcuate length, width, or height measurable within a specified region, portion, feature or area of the implant; e.g., overall arcuate implant length, arcuate width of an anchor arm, arcuate body thickness, or arcuate plate diameter as measured along the path of one or more surfaces, curves, midplanes, or lines of an implant, anchor, body, or plate) and can be categorized as any of constant or variable, continuous or discontinuous, piecewise linear, curvilinear, rectilinear, actual or approximate, across, around, through, or over a section, region, feature, or area of the implant. Arcuate measurements differ from linear measurements in that the arcuate measurements follow a specified path and for curved bodies do not represent the absolute shortest distance between two points.

In certain embodiments, plate width can be measured across a plate at a scleral mating surface, normal to a total implant length. A body width can be measured across a body at a scleral mating surface, normal to a total implant length. An anchor width can be measured across an anchor at a scleral mating surface, normal to a total implant length. Each of implant, body, plate, or anchor thicknesses, respectively, can be measured from a scleral mounting surface normal to total implant length and/or normal to width.

Certain embodiments of the subject invention provide stiff, sturdy, long lasting, inert, one-piece, unbreakable, resilient, tough, or fracture resistant surgical implantable grade material (e.g., titanium or titanium alloy) at a thickness of 0.6 mm to 0.7 mm, alternatively at a thickness of 0.65 mm to 0.75 mm, alternatively at a thickness between 0.5 mm to 0.8 mm, alternatively at a thickness between 0.4 mm to 0.9 mm, alternatively at a thickness between 0.3 mm to 1.0 mm, or increments of any of the foregoing, to provide sufficient thickness for rigidity and robustness with minimal bulk, weight, or discomfort in an implant that can remain in the eye permanently without complication. Alternatively, the implant thickness (e.g., with titanium, other metals, biocompatible polymers, or ceramic materials) can be 0.1 mm, 0.2 mm, 0.3 mm, 0.4 mm, 0.45 mm, 0.55 mm, 0.65 mm, 0.75 mm, 0.8 mm, 0.9 mm, 1.0 mm, 1.1 mm, 1.2 mm, 1.3 mm, 1.4 mm, 1.5 mm, 1.7 mm, or 2 mm, or increments of any of the foregoing. Alternative materials can be employed at differing thickness as appropriate to the material properties of each individual material, in accordance with the teachings of the subject invention.

Compared to more complicated designs, including for example, those wrapping around the eye or having adjustable structures, implants and methods of the subject invention offer the advantages of less complicated design and surgical technique. Thus, embodiments of the subject invention reduce rates of complication, increase surgeon confidence, and improve patient outcomes while reducing risk of damage to the eye's surrounding tissues, nerves, and blood vessels.

In some embodiments the subject invention provides an inner surface of the implant that is concave in its every section and a more natural fit for an eye. The eye is round, and the subject invention provides implants that fit close to the eyeball with a concave surface so that the surface of the retina inside the eye (where the image forms) stays concave. Since the brain has learned to process the information coming from a concave retinal surface, certain embodiments of the subject invention provide advantages over implants with a flat or convex plate facing and touching the eyeball in the back and causing the concavity of the retina inside the eye to be reversed or be flat with the resulting image falling on the retina in a pattern that is unnatural and confusing to the patient. The concavity of the plate offers an advantage after the eyeball is shortened and retraction corrected, the image will still fall on a natural retinal concavity.

In certain embodiments the wider implant body helps ease removal if desired, provides better implant stability, enhanced surgeon handling and confidence, and less risk for dislodgment after the initial placement.

In certain embodiments the subject invention provides a widespread fork-like anterior (front) section with three-point fixation through (e.g., with suture thorough the holes) ensuring the implant will not move right, left or to front and back once placed. The surgical technique of the subject invention is much simpler than other techniques involving larger, more complicated, or less stable implants.

Advantages provided by certain embodiments of the subject invention include fixation without the need to wrap around the eye or pass sensitive structures behind the eyeball (e.g., the optic nerve;) sturdiness with three-point fixation and optional additional fixation on the implant body or additional attachment points; ease of removal if desired; easy intraoperative adjustability to desired AP length, and a simple structure with less irregularity on the implant that helps avoid erosion and exposure after the initial implantation.

In certain embodiments the length of the body will determine how much the implant can shorten the eyeball. The length of the body and curvature radius of the body will determine where the plate will fall and where the anchor structure (e.g., forks) will land in the front of the eye. In some embodiments, a kit with as few as 2 or 3 different standard sizes (alternatively, 4 sizes, or 5 sizes, or 6 sizes) for the body length and/or total implant linear length and/or total implant arcuate length, can be sufficient for a surgeon to serve the majority of their patients by advantageously leveraging intraoperative adjustment together with anterior anchoring to determine the final corrected AP length of the eye. In certain embodiments the size of the plate determines how large of the area at the back of the eye the implant will normalize. It is advantageous for an implant to be small enough to avoid touching or impacting the optic nerve or other structures before, during, and/or after implantation, but large enough to normalize an effective area of the eye. In some embodiments the plate is generally round or cylindrical in shape and has a diameter of 5 mm, alternatively between 4.5 mm and 5.5 mm, alternatively between 4 mm and 6 mm, alternatively between 3.5 mm and 6.5 mm, alternatively between 3 mm and 7 mm, alternatively between 2.5 mm and 7.5 mm, alternatively between 2 mm and 8 mm, alternatively between 1.5 mm and 8.5 mm, alternatively between 1 mm and 9 mm, or increments of any of the foregoing. Alternatively, the plate can have a diameter (or a length, or a width, depending on the shape of the plate) of about 2 mm, or 3 mm, or 4 mm, or 5 mm, or 6 mm, or 7 mm, or 8 mm, or 9 mm, or 10 mm, or increments of any of the foregoing. Alternatively, the plate can be nearly round, oblong, ellipsoid, egg shaped, conical, irregular, or any combination of the above shapes. Alternatively, the plate can have a primary shape and a secondary shape that adds to or subtracts from the primary shape (e.g., a primary circular shape with a secondary ellipsoid cutout, or a primary cylindrical shape with a conical addition.) The sizes discussed above with respect to the diameter of a primary circle or cylinder can apply to secondary shapes as well as primary and can apply to other measurements such as effective or local diameters, chord lengths, widths, or lengths as used to describe the size of the plate relative to the area of the eye to be corrected.

In certain embodiments of the subject invention the implant can have a curvature radius (or radius of curvature) along a scleral mating surface of 14.5 mm in an anterior (e.g., front or anchor) section and a curvature radius (or radius of curvature) along a scleral mating surface of 12.5 mm for the posterior (e.g., rear or plate) section. Alternatively, a radius of curvature at an anterior, posterior, medial, lateral, central, plate, body, anchor, or transitional section of the implant can be 9 mm, 9.5 mm, 10 mm, 10.5 mm, 11 mm, 11.5 mm, 12 mm, 12.5 mm, 13 mm, 13.5 mm, 14 mm, 14.5 mm, 15 mm, 15.5 mm, 16 mm, 16.5 mm, 17 mm, or 17.5 mm, or increments of any of the foregoing. The radius can also be larger than 17.5 mm up to and including a flat or straight section at either end or connecting two other sections of the implant. The radius along any two sections of the implant can be the same or different from each other. The radius along any section of the implant can be constant or variable (e.g., continuously or discontinuously varying along the section) and the transition between any two sections can be smooth, sharp, tangent, continuous, or discontinuous. Two different radius of curvature values can be bridged by a third section transitioning between the two.

With respect to radius of curvature, sections can be defined by numerous features along the length, width, or thickness of the implant, including definition of a section by the radius (or radii) present therein. Radius of curvature can exist in three-dimensional space within the implants of the subject invention and can be measured along any suitable plane or path (e.g., anteroposterior, mediolateral, inferior-superior, front-back, left-right, up-down, or any properly defined plane or path intersection or projecting to or from the implant geometry. At any given point or section of the implant there can exist curvature in more than one direction (e.g., a 14.5 mm radius of curvature in a longitudinal direction can coincide with an 8 mm radius of curvature in a lateral direction.) Radius of curvature can vary across different directions and in different sections of the implant. Smaller or larger radius values can occur in either small, narrow, short sections or large, wide, long sections of the implant.

In addition to transitioning across sections of the implant, radius of curvature can have a different value or end condition at the edge or boundary of a section, feature, or functional part of the implant. For example, the radius can have one value across the macular indenter plate, with a different value (e.g., smaller, larger, opposite, or convex) around the edge of the plate material.

In some embodiments a concave plate with a rolled edge, and/or very small convex rim can reduce trauma or interference with surrounding tissues and/or provide improvements in corrected curvature of the retina, ease of use for the surgeon, and/or comfort for the patient. Certain end, edge, or boundary conditions (e.g., a rolled edge, a convex lip, a rounded periphery, or a smooth and/or tangential transition from a plate to a body and/or and anchor) can beneficially reduce sharpness or potential for cutting and/or damage and/or distortion of the eye by the implant.

In certain embodiments implants according to the subject invention can be made entirely from surgical grade titanium or titanium alloy including smooth, finished, polished and oxidized titanium. Titanium finishing can include oxidizing that turns the meatal color to the well-known titanium blue. Alternatively, the implants can include a secondary material (e.g., silicone or another bioinert or bioactive polymer) applied as a coating, protective layer, or integrated design element (e.g., over-molded, dipped, or sprayed on). A secondary material can be employed as an additional component of a kit or an assembled implant either alone or in a kit (e.g., a silicone bag, mesh, or sleeve) that can be fitted at time of manufacture or by the surgeon at time of implantation and can be permanently affixed, removable, or temporarily removable (e.g., a cover that can be placed on and off the implant until fixed in place by heat-staking, adhesive application, riveting, or similar connection methods known in the art.) Implants can in some cases be worked by machine or by hand to prepare surfaces or edges prior to implantation (e.g., machine tumbling and/or hand polishing during manufacturing.) For example, edges can be chamfered or rounded to a minimum chamfer or radius of 0.1 mm, 0.2 mm, 0.3 mm, 0.4 mm, 0.5 mm, 0.6 mm, 0.7 mm, 0.8 mm, 0.9 mm, or 1 mm, or increments of any of the foregoing.

Certain embodiments of the subject invention advantageously encourage the growth of fibrotic scar tissue over, around, or near the implant by providing a smooth or textured surface, surface coating, surface features, a minimal thickness, rounded or chamfered edges, or a low, moderate, or high width to thickness ratio. In some cases the width to thickness ratio is 7:1, alternatively 20:1, 15:1, 12:1, 10:1, 8:1, 6:1, 4:1, or 2:1 thickness ratio, or increments of any of the foregoing.

In addition to simplified handling and placement at the surgical site, certain embodiments of the subject invention advantageously provide a simple design, easy removal of the implant if desired, and a smooth profile with unitary design (e.g., no mechanical connecting sections that might break or become poorly functional.) These and other features provide a simplified surgical technique including simplified intraoperative adjustment and confirmation of the corrected AP length of the eye (e.g., initially fixing the body of the implant to the sclera can still allow for axial adjustment of the implant to determine desired length and curvature of the eye prior to final fixation and/or anchoring of the implant to the eye.)

The overall implant length can be 20 mm in certain embodiments. The length in certain embodiments can be measured or defined along a linear axis (e.g., linear axial length directly from anterior tip of an anchor to posterior tip of a plate) or along the curved path of an implant (e.g., arcuate length along the curve of the scleral mating surface, or the orbital surface, an implant edge or feature, or a plane or mid-plane of the implant from anterior tip of an anchor to posterior tip of a plate.) Alternatively, the implant length can be 45 mm, 44 mm, 43 mm, 42 mm, 41 mm, 40 mm, 39 mm, 38 mm, 37 mm, 36 mm, 35 mm, 34 mm, 33 mm, 32 mm, 31 mm, 30 mm, 29 mm, 28 mm, 27 mm, 26 mm, 25 mm, 24 mm, 23 mm, 22 mm, 21 mm, 20 mm, 19 mm, 18 mm, 17 mm, or increments of any of the foregoing.

In certain embodiments the anchor can contain a fork structure supporting two or more (e.g., 2, 3, 4, 5, or 6 or more) surgical attachment points. Attachment points and anchor points can be used interchangeably in some embodiments. Alternatively, attachment can refer either to an initial, primary, temporary, and/or adjustable fixation (e.g., loosely suturing an body to a sclera prior to determining the final placement of the implant), or to a final, secondary, permanent, and/or fixed attachment of the implant (e.g., tightly and/or solidly suturing and/or otherwise anchoring an anchor point to a sclera after determining the final placement of the implant).

Fork length (e.g., measured either arcuately or linearly along the direction of a fork) or anchor length (measured either arcuately or linearly along the length of the implant and/or anchor structure) can be between 4 mm and 6 mm, alternatively, fork length or anchor length can be less than 1 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 25 mm, 30 mm, 40 mm, or 45 mm, or increments of any of the foregoing. Fork width (of a single fork) or anchor structure width (of a unitary and/or bifurcated and/or split anchor structural member) can be between 1 mm and 2 mm, and alternatively 0.25 mm, 0.5 mm, 1 mm, 1.5 mm, 2 mm, 2.5 mm, 3 mm, 4 mm, 5 mm, 6 mm, 7 mm, 8 mm, 9 mm, 10 mm, 11 mm, 12 mm, 13 mm, 14 mm, 15 mm, or increments of any of the foregoing.

Body length can be between 15 mm and 20 mm, alternatively 45 mm, 40 mm, 35 mm, 30 mm, 29 mm, 28 mm, 27 mm, 26 mm, 25 mm, 24 mm, 23 mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, 1 mm, or less than 1 mm, or increments of any of the foregoing. Body width can be between 4 mm and 5 mm, alternatively, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm, or increments of any of the foregoing.

Plate diameter (or length, or width, depending on the shape of the plate) can be between 4 mm and 6 mm, alternatively, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm, or increments of any of the foregoing.

Anchor points can include hole or opening sizes between 0.5 mm and 1 mm, alternatively 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.5 mm, 3 mm, 4 mm, 4.5 mm or 5 mm, or increments of any of the foregoing. Anchor points (e.g., two or more holes, each hole at the tip of a respective one of the two or more arms) can be separated by an anchor distance of about 8 mm to about 10 mm apart from each other, alternatively, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm, or increments of any of the foregoing. An anchor distance or anchor width can be defined across any two or more anchor or fastener points.

All implant dimensions mentioned herein can also be taken from ranges about and between the specifically listed individual values (e.g., fork length can be greater than about 3.5 mm and less than about 7.25 mm.)

Certain embodiments can advantageously employ values taken from the available range for different parameters of the implant and can be measured either linearly or along the curvature of the implant. For example, a plate of length 5.5 mm can join with a body of 2 mm and an anchor of 30 mm to form an implant of 37.5 mm length. In some cases, the body length (while still existing) can approach zero or less than 1 mm as the anchor and/or anchor arms evolve from or proximal to the plate itself. In some embodiments the body can be bifurcated or otherwise divided into sections leading into corresponding sections of the anchor and/or anchor arms. Alternatively, a plate of length 5 mm can join with a body of 30 mm and an anchor of 2 mm to form an implant of 37 mm length. In some cases, the anchor length (while still existing) can approach zero or less than 1 mm as the anchor and/or anchor arms evolve from or proximal to the anterior end of the body itself. In some embodiments the anchor can be monolithic or of a single shape. Alternatively, the anchor can be bifurcated or otherwise divided into sections leading into corresponding sections of the body and/or a single body section. Alternatively, in certain embodiments the anchor extends directly from the plate (i.e., there can be no body.) In certain embodiments the implant has no anchor; the anchor is the same or lesser width compared to the body; and/or the implant is anchored directly from, through, or around the body.

In certain embodiments a light, compact, and simple implant design is advantageously applied to provide smooth uncomplicated and gentle surgery to produce stable fixation while reducing risks such as thin tissue at the eyewall of the patient bringing a chance to rupture at any part of it. The design including a stable base of the implant plate and body together with progressive placement and anchoring that proceeds from the body to the anchor points and allows for planned and controlled intraoperative adjustments during the process of progressive placement and anchoring. Correct measurements of exactly where to place the implant (e.g., pre-surgical measurements and intra-operative measurements) further aid in reduction of risk and improve patient outcomes.

In myopia, front to back (anteroposterior AP) length of the eye is increased. AP length of the eye is normally 22 mm to 24 mm (average 23 mm). Each mm additional elongation gives 3 diopters of refractive error to the eye. In the case where the AP length is 26 mm (approximately 2 mm longer than normal), the patient is (2×3D)–6.00 myopic. When the AP length is longer than normal, the contents of the eyeball will stretch to fit the larger space created inside. One structure inside the eye that ends up stretching to fit is the retina. The retina includes a nerve layer inside that makes the picture and sends it to the brain. The retina covers the inside of the back of the eye like a wallpaper covering a wall. In the case of the wall of the eye bulging out in the back of the eye, the wallpaper inside can stretch and tear in the middle. In the case of an actual eye, this tear can be in the form of a round hole right in the center, a macular hole. Surgeons call this condition macular hole in a high myopic eye. Macular holes can also happen in normal length eyes. One surgery to treat a macular hole requires placement of a bubble inside the eye to push that hole closed by asking the patient to keep her or his head down so that the floating bubble will push the hole closed. In the case of high myopia, the retina is so stretched that the hole will not easily close. The patient chance of success is better if the wall of the eye is pushed in from the outside in accordance with the subject invention. Placing an implant to bring the wall of the eye forward in accordance with the subject invention will increase the chance of closure of the macula hole following intraocular surgery to treat a macular hole.

Advantages of the subject invention include ease to manufacture and implant, but also put simply, the eye can handle a simpler design better. By reduction of mechanical components and connections and electronics, the subject invention reduces complication and risk to place and maintain an implant for decades in the eye. Better outcomes are facilitated with an easier, simpler design. Surgical technique is simpler and less challenging with a simpler one-piece design. The implants and methods of the subject invention offer greater accessibility for a retina specialist, or some other subspecialists in the field of ophthalmology having the ability to pass a suture on the sclera (i.e., the white part, outer coat of the eye). Retina surgeons and strabismus surgeons are familiar with the technique of passing sutures in the sclera in a manner adaptable to the surgical techniques of the subject invention.

One application of certain embodiments of the subject invention is to shorten the axial length of the eye to correct myopia (near-sightedness). Certain embodiments can be used to correct hyperopia (far-sightedness) and/or astigmatism (the eye being in the shape of a football or an egg, rather than a regular round ball). One embodiment as shown on FIG. 1 can be described as a "J" shaped stent having a plate on one end and a "Y" shaped fork on the other end. In certain embodiments, the designed length of the stent can vary based on the size of the eye of an intended patient.

The diagram in FIG. 2 shows one representative and non-limiting embodiment attached in the eye after surgery. In the case of myopia, when the eye is longer than normal, the device can pull the back of the eye forward to make the eye shorter, and the device can be sutured on the side of an eye with 3 holes on the 2 ends of the "Y" and at the location where the Y fork meets the body. Additional holes can be made on the device for additional suturing of the device on the eye. In some embodiments, holes can be placed on the anchor, the body, or the plate of the implant. In addition to holes, certain embodiments can advantageously employ protrusions, notches, ridges, slots, bumps, arms, depression, grooves, or other attachments as known in the art and as appropriate for the fasteners (e.g., sutures or staples) employed.

Certain embodiments of the subject invention provide a surgical implant (100) for changing the axial length of an eye, with a plate (110) located at a posterior end of the implant, an anchor (130) located at an anterior end of the implant, an elongate body (120) having a body length extending between the anchor and the plate, a concave scleral surface (140) extending from the posterior end of the implant to the anterior end of the implant, connecting the plate, the body, and the anchor. The implant can also have a convex orbital surface (150) opposite the scleral surface, and a pair of opposing lateral sides (160) connecting the orbital surface and the scleral surface along at least a portion of the body length, the scleral surface having a posterior radius of curvature (R1) in a region proximate the posterior end, and an anterior radius of curvature (R2) in a region proximate the anterior end, the posterior radius being smaller than the anterior radius. The plate can have a shape that defines a plate width (PW) at the scleral surface. The elongate body can have a shape that defines a body width (BW) between opposing lateral sides at the scleral surface. The anchor can have two suture portals (131A, 131B) extending from the scleral surface to the orbital surface and defining an anchor width (AW) therebetween, the body width being at least about ⅔ of the plate width, and the anchor width being greater than the body width.

In certain embodiments, the surgical application site can be at the exterior of the eye as shown in FIG. 2. Looking at an eye from the front, there are 4 major straight muscles that move the eye up, down, right, and left. The fixation of these muscles is at approximately 12 o'clock (superior rectus muscle), 3 o'clock (lateral rectus if it's the right eye, and medial rectus if it's the left eye), 6 o'clock (inferior rectus muscle), and 9 o'clock (medial rectus if it's the right eye, and lateral rectus if it's the left eye), positions. The muscles are not visible from the outside of the eye. These muscles typically start 6-7 mm behind the limbus (i.e., where the cornea meets the sclera, the circular edge where the white sclera starts when viewing an eye). The sections of eye between these four muscles can be referred to as quadrants. Although the implant can be placed in any quadrant (inferonasal, superonasal, inferotemporal, superotemporal), inferotemporal quadrant (outer bottom), and superotemporal (outer upper) offer easy access and less potential risk of touching the optic nerve while placing the implant. Certain embodiments of the subject invention provide implants configured and adapted to avoid the optic nerve that can be partially in the way of an implant placed in the superonasal (inner upper) and inferonasal (inner bottom) quadrants for cases where the temporal quadrants are too scarred (e.g., from a previous surgery or trauma.) Surgical placement of implants in the temporal quadrants will have reduced risk to the important structures (e.g., the optic nerve and/or veins) in accordance with certain embodiments of the subject invention. Retina surgeons are very familiar in accessing these quadrants under the conjunctiva (i.e., the skin of the eyeball). Retina surgeons commonly place silicone implants for retinal detachment repair in those quadrants on the sclera, by passing half thickness sutures in the sclera. Bluntly dissecting these quadrants will give access to the wall of the eye without damaging the nerves and the blood vessels. In certain embodiments the implant of the subject invention having a blunt edge will be easily placed without damaging the critical structures while following a surgical approach and technique familiar to ophthalmic surgeons. In certain embodiments the implant of the subject invention provides a simple, compact, and stable attachment to the delicate structures of the eye within the bounds of surrounding tissues.

In certain embodiments the implant will be positioned vertically (and posteriorly) from the limbus of the patient's eye (e.g., extending above the limbus towards the back of the eye.) The plate will be inserted backwards (e.g., by passing the plate first, then the body, and finally the anchor through the incision) to support the back of the eye and pull it forward. In certain embodiments a Y shaped fork with the holes will be fixated at about approximately 3-10 mm behind the limbus and covered with patient's own conjunctiva after fixating and anchoring the implant at a desired depth. In cases where the patient's own sclera is too thin, a scleral patch (e.g., a processed donor sclera such as TUTOPLAST®) can be paced over the implant, under the conjunctiva. The body of the implant can be initially placed on the eyeball with nonabsorbable stitches (e.g., MERSILENE® Polyester Fiber Suture, available from J&J Ethicon, Cincinnati, OH).

In certain embodiments, the final implant position can be determined by anchoring the anchor arms on the eyeball after the desired shortening is determined by the surgeon pulling the implant forward to pushing it back after the initial placement and fixation of the body on the eyeball (e.g., with sutures). The desired shortening and shape change of the eye can be determined either by measuring the AP length intraoperatively and adjusting during the placement (e.g., using an OCULAR RESPONSE ANALYZER® (ORA) device, Reichert, Inc., Depew, NY) or referring to a nomogram (e.g., referring to a chart of previously collected data).

The subject invention provides a surgical path that is easily formed, making the surgery simple for a retina specialist or for a surgeon who is familiar with placing sutures on the sclera to place scleral implant or a retinal detachment repair (e.g., a retina specialists) and surgeons doing surgery for strabismus (e.g., surgeons with experience cutting eye muscles and stitching them back on the sclera. In some embodiments the surgery will require cutting the conjunctiva to access the sclera in the desired quadrant. A blunt backwards dissection like a tunnel scraping against the sclera will make the nest or implant location for the implant. The implant will be placed at this location and the body will be first fixated on the eyeball (e.g., using a suture). Since it can still be possible to pull or push the implant sliding the body within the initial attachment, the surgeon can adjust anteroposterior positioning, determine where to fixate the anterior anchor section (e.g., with additional sutures through the holes). Conjunctiva can be sutured over the implant with or without a biologic covering (e.g., TUTOPLAST®) over the implant.

Definitions

In order that the present disclosure can be more readily understood, certain terms are defined below, and throughout the detailed description, to provide guidance as to their meaning as used herein.

As used herein, the terms "a," "an," "the" and similar terms used in the context of the present invention are to be construed to cover both the singular and plural unless otherwise indicated herein or clearly contradicted by the context. Thus, for example, reference to "an arm" or "a hole" should be construed to cover or encompass both a singular arm or a singular hole and a plurality of arms and a plurality of holes, unless indicated otherwise or clearly contradicted by the context.

As used herein, the terms "about" and "approximately" shall generally mean an acceptable degree of error for the quantity measured given the nature or precision of the measurements. Exemplary degrees of error are within 20 percent (%), typically, within 10%, and more typically, within 5% of a given value or range of values. As used herein, the term "and/or" should be understood to mean "either or both" of the features so conjoined, i.e., elements that are conjunctively present in some cases and disjunctively present in other cases.

As used herein, the terms "comprising", "consisting of" and "consisting essentially of" are defined according to their standard meaning. The terms can be substituted for one another herein in order to attach the specific meaning associated with each term.

As used herein, the term "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "patient" and "subject" are used interchangeably herein to refer to a human or non-human animal.

As used herein, the terms "device" and "implant" are used interchangeably herein (e.g., in reference to an ophthalmic surgical implant or staphyloma supporting device) unless expressly distinguished.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Prospective Surgical Case Study

In this prospective surgical case study, an extremely near-sighted (myopic) patient presented with a failed macular hole surgery previously. In this patient the tear was in the form of a round hole right in the center, a macular hole in a high myopic eye. The prospective surgery for macular hole requires that we place a bubble inside the eye and push that hole closed by asking the patient to keep her or his head down so that the floating bubble will push the hole closed. In the case of high myopia, the retina can be so stretched that the hole will not easily come close. The patient had such as surgery before and the hole had not closed. The patient's chance of success would be much better if the wall of the eye was pushed in from the outside. Placing an implant to bring the wall of the eye forward would increase the chance of closure of the macula hole.

Total AP length measured for this patient was about 30 mm. Based on preoperative measurements, an implant in accordance with the subject invention was designed by the inventor and manufactured (Total Titanium Inc., Red Bud, IL). A circular plate of 6 mm diameter joined to a body of 5 mm width and an anchor of 12 mm width in the form of a symmetric Y with two arms supporting two anterior fixation points with at third central fixation point at the neck of the Y proximal to the body. All fixation points were 1 mm diameter through holes for suture attachment. The implant was manufactured from 6AL-4EV-ELI Titanium flat sheet stock of uniform 0.7 mm thickness. Prior to bending the radius of curvature into the scleral contact surface, the flat pattern length of the implant was 30.5 mm and the flat pattern length of the anchor section was 5 mm. After bending the radius of curvature into the scleral contact surface, the arcuate length of the implant was about 30.5 mm and the arcuate length of the anchor section was 5 mm. The posterior radius of curvature was 12.5 mm, the anterior radius of curvature was 14.5 mm and the two curvatures met in a tangent surface condition along a line 14 mm from the anterior edge of the flat pattern blank and 16.5 mm from the posterior edge of the flat pattern blank. The resulting implant AP length, measured in a straight line from posterior edge of the scleral contact surface at the plate to anterior edge of the scleral contact surface at the anchor, was approximately 24 mm.

Example 2—Actual Surgical Case Study

In this actual surgical case study the objective was to introduce a new design for an easy to place titanium staphyloma supporting device (also referred to as a macular implant or staphyloma supporting implant) and the surgical technique for placing it in myopic macular holes.

A 60-year-old patient with degenerative myopia presented with macular hole in both eyes. The macular hole in the right eye was a recurrent long-standing hole over 5 years from the initial diagnosis. The patient refused surgery for the better seeing left eye. The right eye vision was 20/400.

In the absence of a commercially available staphyloma supporting device, a custom-made titanium implant was designed and manufactured for this patient (as shown in FIG. 7). In addition to the standard pars plana vitrectomy, internal limiting membrane peel, and gas tamponade, the titanium staphyloma supporting device was placed externally to provide indentation over the macula.

The titanium staphyloma supporting device provided 1 mm of indentation, shortening the axial length from 28.88 mm to 27.94 mm. The macular hole was closed postoperatively. Postoperative best corrected visual acuity was 20/400 at 1 month with no complications from the titanium staphyloma supporting device or the surgical technique.

A preoperative optical coherence tomography (OCT) and a postoperative OCT were recorded. The tip of the implant was seen in the postoperative OCT just underneath the macular indentation.

This surgical case study demonstrates that a titanium staphyloma supporting device in accordance with the subject invention can be advantageously applied for the surgical repair of degenerative myopic macular pathologies, including myopic macular holes.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

I claim:

1. A staphyloma supporting implant for improving vision and/or refractive power of the eye in a patient by restoring the natural curvature and natural axial length of an eye and/or shortening the axial length of the eye, the staphyloma supporting implant comprising:
- a plate having a concave scleral mating surface configured to restore the natural curvature of a posterior portion of the eye;
- an anchor having a concave scleral mating surface configured to approximate the natural curvature of an anterior portion of the eye; and
- an elongated body having a continuous and smooth concave scleral mating surface connecting the plate to the anchor;
- the eye having a natural axial length and the implant having a total implant length less than the natural axial length of the eye;
- the body having a body width;
- the plate having a plate width;
- the body width being less than the plate width;
- the anchor having an anchor width;
- the anchor width being greater than the body width;
- the anchor width being less than three times the plate width;
- the anchor comprising:
  - a first anchor point central to the body,
  - a second anchor point medial to the body and either anterior or posterior to the first anchor point,
  - a third anchor point lateral to the body and either anterior or posterior to the first anchor point,
  - a first arm connecting the second anchor point to the body, the first arm having an arm width less than the body width, and
  - a second arm connecting the third anchor point to the body, the second arm having an arm width less than the body width;
- the plate having a first radius of curvature (RP);
- the anchor having a second radius of curvature (RA);
- the first radius of curvature being greater than the second radius of curvature (RP>RA);
- the body having a first radius of curvature (RB1) proximate the plate;
- the body having a second radius of curvature (RB2) proximate the anchor;
- the first radius of curvature of the body being greater than the second radius of curvature of the body (RB1>RB2);
- the body having a transition of curvature that maintains surface tangency between the first radius of curvature of the body (RB1) and the second radius of curvature of the body (RB2),
- wherein the first arm and the second arm form a Y shape with respect to the body; and
- wherein the plate, the body, and the anchor are monolithically-formed.

2. The staphyloma supporting implant of claim 1, further defined by:
   the implant comprising one or more polymers selected from the group consisting of ultra-high molecular-weight polyethylene (UHMWP), high-density polyethylene (HDP), polymethyl methacrylate (PMMA) or other methacrylates, silicone (polysiloxanes), and VICRYL® (polyglactin 910).

3. The staphyloma supporting implant of claim 1, further defined by:
   the implant comprising one or more metals selected from the group consisting of surgical grade stainless steel, cobalt-chromium (Co—Cr) alloys, pure commercial or surgical grade titanium (Ti), nickel-titanium alloy (nitinol), and other titanium alloys.

4. The staphyloma supporting implant of claim 3, wherein the metal is either surgical grade titanium or a surgical grade titanium alloy.

5. The staphyloma supporting implant of claim 4, further defined by:
   the implant made entirely from surgical grade titanium or titanium alloy finished with an oxidizing that turns the metal color to titanium blue.

6. The staphyloma supporting implant of claim 3, further defined by:
   the metal having a modulus of elasticity between 105 gigapascals (GPa) and 193 Gpa.

7. The staphyloma supporting implant of claim 1, further defined by:
   the implant comprising one or more metals selected from the group consisting of gold, platinum, silver, iridium, tantalum, and tungsten.

8. The staphyloma supporting implant of claim 1, further defined by:
   each of the first anchor point, the second anchor point, and the third anchor point, respectively, comprising a 0.5 mm to 3 mm diameter through hole for suture attachment.

9. The staphyloma supporting implant of claim 1, further defined by:
   an arcuate length of the implant being between 28 mm and 45 mm and an arcuate length of the anchor being between 5 mm and 10 mm; and
   the total implant axial length being between 20 mm and 34 mm.

10. The staphyloma supporting implant of claim 1, further defined by:
    the implant having a uniform thickness of 2 mm or less;
    the first radius of curvature (RB1) being greater than 10 mm and less than 20 mm; and
    the second radius of curvature (RB2) being less than 10 mm and greater than 6 mm.

11. The staphyloma supporting implant of claim 1, further defined by:
    the implant comprising one or more ceramics selected from the group consisting of aluminum oxide, calcium phosphates, zirconium oxide (Zirconia), and silicon oxide (Silica).

12. The staphyloma supporting implant of claim 1, further defined by:
    the implant comprising one or more natural or synthetic biological materials selected from the group consisting of autograft, allograft, xenograft, synthetic tissue substitutes, and cultured or engineered tissues or tissue substitutes.

13. The staphyloma supporting implant of claim 1, further defined by:
    the plate being a circular plate having a diameter between 1 mm and 9 mm;
    the body width being less than 5 mm; and
    the anchor width being between 5 mm and 15 mm.

14. The staphyloma supporting implant of claim 13, further defined by:
    the Y shape being symmetric with respect to the body.

15. A staphyloma supporting implant for improving vision in a patient by restoring the natural curvature and natural axial length of an eye, the staphyloma supporting implant comprising:
    a plate having a concave scleral mating surface configured to restore the natural curvature of a posterior portion of the eye;

an anchor having a concave scleral mating surface configured to approximate the natural curvature of an anterior portion of the eye; and an elongated body having a continuous and smooth concave scleral mating surface connecting the plate to the anchor;

the eye having a natural axial length and the implant having a total implant length less than the natural axial length of the eye;

the body having a body width;
the plate having a plate width;
the body width being less than the plate width;
the anchor having an anchor width;
the anchor width being greater than the body width;
the anchor width being less than three times the plate width;
the anchor comprising:
   a first anchor point central to the body,
   a second anchor point medial to the body and either anterior or posterior to the first anchor point,
   a third anchor point lateral to the body and either anterior or posterior to the first anchor point,
a first arm connecting the second anchor point to the body, the first arm having an arm width less than the body width, and
a second arm connecting the third anchor point to the body, the second arm having an arm width less than the body width;
the plate having a first radius of curvature (RP);
the anchor having a second radius of curvature (RA);
the first radius of curvature being greater than the second radius of curvature (RP>RA);
the body having a first radius of curvature (RB1) proximate the plate;
the body having a second radius of curvature (RB2) proximate the anchor;
the first radius of curvature of the body being greater than the second radius of curvature of the body (RB1>RB2);
the body having a transition of curvature that maintains surface tangency between the first radius of curvature of the body (RB1) and the second radius of curvature of the body (RB2);
wherein the first arm and the second arm form a Y shape with respect to the body; and
wherein the plate, the body, and the anchor are monolithically-formed from a metal that is either surgical grade titanium or a surgical grade titanium alloy having a modulus of elasticity between 105 gigapascals (GPa) and 193 Gpa.

16. The staphyloma supporting implant of claim 15, further defined by:
an arcuate length of the implant being between 28 mm and 45 mm and an arcuate length of the anchor being between 5 mm and 10 mm; and
the total implant axial length being between 20 mm and 34 mm.

17. The staphyloma supporting implant of claim 16, further defined by:
the implant having a uniform thickness of 2 mm or less;
the first radius of curvature (RB1) being greater than 10 mm and less than 20 mm; and
the second radius of curvature (RB2) being less than 10 mm and greater than 6 mm.

18. The staphyloma supporting implant of claim 15, further defined by:
the plate being a circular plate having a diameter between 1 mm and 9 mm;
the body width being less than 5 mm; and
the anchor width being between 5 mm and 15 mm.

19. The staphyloma supporting implant of claim 18, further defined by:
the Y shape being symmetric with respect to the body; and
wherein the surgical grade titanium or titanium alloy is finished with an oxidizing that turns the metal color to titanium blue.

20. A staphyloma supporting implant for improving vision in a patient by restoring the natural curvature and natural axial length of an eye, the staphyloma supporting implant comprising:
a plate having a concave scleral mating surface configured to restore the natural curvature of a posterior portion of the eye;
an anchor having a concave scleral mating surface configured to approximate the natural curvature of an anterior portion of the eye; and
an elongated body having a continuous and smooth concave scleral mating surface connecting the plate to the anchor;
the eye having a natural axial length and the implant having a total implant length less than the natural axial length of the eye;
the body having a body width;
the plate having a plate width;
the body width being less than the plate width;
the anchor having an anchor width;
the anchor width being greater than the body width;
the anchor width being less than three times the plate width;
the anchor comprising:
   a first anchor point central to the body,
   a second anchor point medial to the body and either anterior or posterior to the first anchor point,
   a third anchor point lateral to the body and either anterior or posterior to the first anchor point,
a first arm connecting the second anchor point to the body, the first arm having an arm width less than the body width, and
a second arm connecting the third anchor point to the body, the second arm having an arm width less than the body width;
the plate having a first radius of curvature (RP);
the anchor having a second radius of curvature (RA);
the first radius of curvature being greater than the second radius of curvature (RP>RA);
the body having a first radius of curvature (RB1) proximate the plate;
the body having a second radius of curvature (RB2) proximate the anchor;
the first radius of curvature of the body being greater than the second radius of curvature of the body (RB1>RB2);
the body having a transition of curvature that maintains surface tangency between the first radius of curvature of the body (RB1) and the second radius of curvature of the body (RB2);
wherein the first arm and the second arm form a symmetric Y shape with respect to the body;
wherein the plate, the body, and the anchor are monolithically-formed from a metal that is either surgical grade titanium or a surgical grade titanium alloy having a modulus of elasticity between 105 gigapascals (GPa) and 193 Gpa;
an arcuate length of the implant being between 30 mm and 32 mm and an arcuate length of the anchor being between 6 mm and 8 mm;

the total implant length being between 20 mm and 25 mm;
the implant having a uniform thickness of 1 mm or less;
the first radius of curvature of the body (RB1) being greater than 11 mm and less than 13 mm;
the second radius of curvature of the body (RB2) being less than 11 mm and greater than 9 mm;
the plate being a circular plate having a diameter between 6 mm and 8 mm;
the body width being between 2 mm and 5 mm; and
the anchor width being between 5 mm and 8 mm.

\* \* \* \* \*

UNITED STATES PATENT AND TRADEMARK OFFICE
CERTIFICATE OF CORRECTION

PATENT NO. : 12,070,387 B2
APPLICATION NO. : 18/359744
DATED : August 27, 2024
INVENTOR(S) : Levent Akduman Page 1 of 1

It is certified that error appears in the above-identified patent and that said Letters Patent is hereby corrected as shown below:

In the Specification

Column 11:
Line 13, "alternatively, less than degrees" should read --alternatively, less than 30 degrees--

Signed and Sealed this
Seventh Day of October, 2025

John A. Squires
*Director of the United States Patent and Trademark Office*